US012220467B2

(12) United States Patent
Stewart et al.

(10) Patent No.: US 12,220,467 B2
(45) Date of Patent: *Feb. 11, 2025

(54) HIGHLY LOADED METAL OXIDE MATERIALS BY SELF-ASSEMBLY FOR EXTENDED BIOLOGICALLY ACTIVE MOLECULE RELEASE IN MEDICAL AND DENTAL APPLICATIONS

(71) Applicant: MESOSIL INC., Toronto (CA)

(72) Inventors: Cameron Alexander Stewart, Springwater (CA); Benjamin David Hatton, Toronto (CA); Yoav Finer, Toronto (CA)

(73) Assignee: MESOSIL INC., Toronto (CA)

( * ) Notice: Subject to any disclaimer, the term of this patent is extended or adjusted under 35 U.S.C. 154(b) by 301 days.

This patent is subject to a terminal disclaimer.

(21) Appl. No.: 17/463,002

(22) Filed: Aug. 31, 2021

(65) Prior Publication Data

US 2022/0000722 A1 Jan. 6, 2022

Related U.S. Application Data

(63) Continuation of application No. 16/301,773, filed as application No. PCT/CA2017/050586 on May 16, 2017, now Pat. No. 11,129,774.

(Continued)

(51) Int. Cl.
*A61K 6/84* (2020.01)
*A01N 25/08* (2006.01)
(Continued)

(52) U.S. Cl.
CPC ............... *A61K 6/84* (2020.01); *A01N 25/08* (2013.01); *A01N 43/40* (2013.01); *A01N 47/44* (2013.01);
(Continued)

(58) Field of Classification Search
CPC ... A61K 6/84; A61K 6/20; A61K 6/35; A61K 6/40; A61K 6/54; A61K 6/71; A61K 6/74;
(Continued)

(56) References Cited

U.S. PATENT DOCUMENTS 6,027,666 A  2/2000 Ozin et al.
7,172,770 B2 2/2007 Ma et al.
(Continued)

FOREIGN PATENT DOCUMENTS

CN    103655207 A  *  3/2014  ............. A61K 31/43
WO    2005110592 A1    11/2005
WO    2007108016 A1    9/2007

OTHER PUBLICATIONS

Altunsoy et al. (J Appl Biomater Funct Mater 2015; 13(2): e100-e105). (Year: 2015).*

(Continued)

*Primary Examiner* — Ernst V Arnold

(57) ABSTRACT

A biocompatible composite material for controlled release is disclosed, comprising a biocompatible metal oxide structure with a loaded network of pores. The pore network of the biocompatible composite material is filled with a uniformly distributed biologically active micellizing amphiphilic molecule, the size of these pores ranging from about 0.5 to about 100 nanometers. The material is characterized in that when exposed to phosphate-buffered saline (PBS), the controlled release of the active amphiphilic molecule is predominantly diffusion-driven over time.

3 Claims, 15 Drawing Sheets

Related U.S. Application Data

(60) Provisional application No. 62/337,016, filed on May 16, 2016.

(51) Int. Cl.

| | | |
|---|---|---|
| A01N 43/40 | (2006.01) |
| A01N 47/44 | (2006.01) |
| A61K 6/20 | (2020.01) |
| A61K 6/35 | (2020.01) |
| A61K 6/40 | (2020.01) |
| A61K 6/54 | (2020.01) |
| A61K 6/71 | (2020.01) |
| A61K 6/74 | (2020.01) |
| A61K 6/76 | (2020.01) |
| A61K 6/80 | (2020.01) |
| A61K 6/802 | (2020.01) |
| A61K 6/849 | (2020.01) |
| A61K 6/853 | (2020.01) |
| A61K 6/86 | (2020.01) |
| A61K 6/864 | (2020.01) |
| A61K 6/871 | (2020.01) |
| A61K 9/00 | (2006.01) |
| A61K 9/14 | (2006.01) |
| A61K 9/51 | (2006.01) |
| A61K 31/155 | (2006.01) |
| A61K 31/20 | (2006.01) |
| A61K 31/4425 | (2006.01) |
| A61K 31/444 | (2006.01) |
| A61K 31/785 | (2006.01) |
| A61L 27/02 | (2006.01) |
| A61L 27/10 | (2006.01) |
| A61L 27/12 | (2006.01) |
| A61L 27/30 | (2006.01) |
| A61L 27/32 | (2006.01) |
| A61L 27/42 | (2006.01) |
| A61L 27/44 | (2006.01) |
| A61L 27/54 | (2006.01) |
| A61L 27/56 | (2006.01) |
| A61P 1/02 | (2006.01) |
| A61P 31/02 | (2006.01) |
| A61P 31/04 | (2006.01) |
| C07C 279/14 | (2006.01) |
| C07C 279/26 | (2006.01) |
| C07D 213/20 | (2006.01) |
| C07D 213/74 | (2006.01) |
| C08K 3/22 | (2006.01) |
| C08K 3/32 | (2006.01) |
| C08L 33/10 | (2006.01) |
| C08L 33/12 | (2006.01) |
| C08L 75/04 | (2006.01) |

(52) U.S. Cl.
CPC .......... *A61K 6/20* (2020.01); *A61K 6/35* (2020.01); *A61K 6/40* (2020.01); *A61K 6/54* (2020.01); *A61K 6/71* (2020.01); *A61K 6/74* (2020.01); *A61K 6/76* (2020.01); *A61K 6/80* (2020.01); *A61K 6/802* (2020.01); *A61K 6/849* (2020.01); *A61K 6/853* (2020.01); *A61K 6/86* (2020.01); *A61K 6/864* (2020.01); *A61K 6/871* (2020.01); *A61K 9/0024* (2013.01); *A61K 9/0063* (2013.01); *A61K 9/143* (2013.01); *A61K 9/5115* (2013.01); *A61K 31/155* (2013.01); *A61K 31/20* (2013.01); *A61K 31/4425* (2013.01); *A61K 31/444* (2013.01); *A61K 31/785* (2013.01); *A61L 27/025* (2013.01); *A61L 27/10* (2013.01); *A61L 27/105* (2013.01); *A61L 27/12* (2013.01); *A61L 27/306* (2013.01); *A61L 27/32* (2013.01); *A61L 27/425* (2013.01); *A61L 27/427* (2013.01); *A61L 27/446* (2013.01); *A61L 27/54* (2013.01); *A61L 27/56* (2013.01); *A61P 1/02* (2018.01); *A61P 31/02* (2018.01); *A61P 31/04* (2018.01); *C07C 279/14* (2013.01); *C07C 279/26* (2013.01); *C07D 213/20* (2013.01); *C07D 213/74* (2013.01); *C08K 3/22* (2013.01); *C08K 3/32* (2013.01); *C08L 33/12* (2013.01); *A61L 2300/206* (2013.01); *A61L 2300/208* (2013.01); *A61L 2300/404* (2013.01); *C08K 2003/2227* (2013.01); *C08K 2003/2237* (2013.01); *C08K 2003/2296* (2013.01); *C08K 2003/325* (2013.01); *C08L 2203/02* (2013.01)

(58) Field of Classification Search
CPC . A61K 6/76; A61K 6/80; A61K 6/802; A61K 6/849; A61K 6/853; A61K 6/86; A61K 6/864; A61K 6/871; A61K 9/0024; A61K 9/0063; A61K 9/143; A61K 9/5115; A61K 31/155; A61K 31/20; A61K 31/4425; A61K 31/444; A61K 31/785; A01N 25/08; A01N 43/40; A01N 47/44; A61L 27/025; A61L 27/10; A61L 27/105; A61L 27/12; A61L 27/306; A61L 27/32; A61L 27/425; A61L 27/427; A61L 27/446; A61L 27/54; A61L 27/56; A61L 2300/206; A61L 2300/208; A61L 2300/404; A61P 1/02; A61P 31/02; A61P 31/04; C07C 279/14; C07C 279/26; C07D 213/20; C07D 213/74; C08K 3/22; C08K 3/32; C08K 2003/2227; C08K 2003/2237; C08K 2003/2296; C08K 2003/325; C08L 33/12; C08L 2203/02

See application file for complete search history.

(56) References Cited

U.S. PATENT DOCUMENTS

| | | | |
|---|---|---|---|
| 7,611,731 | B2 | 11/2009 | Wyrsta et al. |
| 8,790,697 | B2 | 7/2014 | Martens et al. |
| 11,129,774 | B2* | 9/2021 | Stewart .............. A61P 31/04 |
| 2002/0197206 | A1 | 12/2002 | Balkus et al. |
| 2004/0228787 | A1 | 11/2004 | Loureiro et al. |
| 2006/0018966 | A1* | 1/2006 | Lin .............. A61K 9/2081 514/358 |
| 2006/0263444 | A1* | 11/2006 | Ming ............ A01N 47/44 424/641 |
| 2007/0249744 | A1 | 10/2007 | Landskron et al. |

OTHER PUBLICATIONS

Muller et al. (Journal of Antimicrobial Chemotherapy 2008;61:1281-1287) (Year: 2008).*

Melo et al. (Dent Mater. 2013;29(2):199-201). (Year: 2013).*

Google Dictionary "system" retrieved on Jan. 12, 2024; 1 page. (Year: 2024).*

Octenidine dihydrochloride [online] retrieved on Jul. 16, 2024 from: https://www.chemicalbook.com/ChemicalProductProperty_US_CB7879838.aspx; 4 pages. (Year: 2024).*

English translation of CN103655207A; 2014; 11 pages (Year: 2014).*

Izquierdo-Barba et al., "Incorporation of Antimicrobial Compounds in Mesoporous Silica Film Monolith," Biomaterials, 2009, vol. 30(29), pp. 5729-5736.

(56) References Cited

OTHER PUBLICATIONS

Carpenter et al., "O2-protected Diazeniumdiolate-modified Silica Nanoparticles for Extended Nitric Oxide Release From Dental Composites," Biomaterials Science, 2013, vol. 1(5), pp. 456-459.
Chang et al., "Polydopamine-based Surface Modification of Mesoporous Silica Nanoparticles as pH-sensitive Drug Delivery Vehicles for Cancer Therapy," Journal of Colloid and Interface Science, 2016, pp. 279-287.
Fontecave et al., "Using Evaporation-induced Self-assembly for the Direct Drug Templating of Therapeutic Vectors With High Loading Fractions, Tunable Drug Release, and Controlled Degradation," Chemistry of Materials, 2013, vol. 25(23), pp. 4671-4678.
He et al., "A pH-responsive Mesoporous Silica Nanoparticles-based Multi-drug Delivery System for Overcoming Multi-drug Resistance," Biomaterials, 2011, vol. 32, pp. 7711-7720.
He et al., "An Anticancer Drug Delivery System Based on Surfactant-templated Mesoporous Silica Nanoparticles," Biomaterials, 2010, vol. 31(12), pp. 3335-3346.
International Patent Application No. PCT/CA2017/050586, International Search Report and Written Opinion dated Sep. 14, 2017.
Jia et al., "Multifunctional Mesoporous Silica Nanoparticles Mediated Co-delivery of Paclitaxel and Tetrandrine for Overcoming Multidrug Resistance," International Journal of Pharmaceutics, 2015, vol. 1-2, pp. 318-330.
Kobayashi et al., "Molecular Ordering of Mixed Surfactants in Mesoporous Silicas: A Solid-state NMR Study," Solid State Nuclear Magnetic Resonance, 2011, vol. 39(3-4), pp. 65-71.
Lee et al., "Development of Long-term Antimicrobial Poly(Methyl Methacrylate) by Incorporating Mesoporous Silica Nanocarriers," Dental Materials : Official Publication of the Academy of Dental Materials, 2016, vol. 32(12), pp. 1564-1574.
Morales et al., "New Drug-structure-directing Agent Concept: Inherent Pharmacological Activity Combined With Templating Solid and Hollow-shell Mesostructured Silica Nanoparticles," Advanced Functional Materials, 2016, pp. 7291-7303.
Muller et al., "Biocompatibility Index of Antiseptic Agents by Parallel Assessment of Antimicrobial Activity and Cellular Cytotoxicity," Journal of Antimicrobial Chemotherapy, 2008, vol. 61(6), pp. 1281-1287.
Trewyn et al., "Morphological Control of Room-temperature Ionic Liquid Templated Mesoporous Silica Nanoparticles for Controlled Release of Antibacterial Agents," Nano Letters, American Chemical Society, vol. 4, 2004, pp. 2139-2143.
U.S. Appl. No. 16/301,773, Restriction Requirement dated Nov. 27, 2019.
U.S. Appl. No. 16/301,773, Notice of Allowance dated Jun. 9, 2021.
U.S. Appl. No. 16/301,773, Advisory Action dated Dec. 22, 2020.
U.S. Appl. No. 16/301,773, Final office Action dated Sep. 14, 2020.
U.S. Appl. No. 16/301,773, Non Final office Action dated Jan. 27, 2021.
U.S. Appl. No. 16/301,773, Non Final office Action dated Mar. 6, 2020.
Zhang et al., "Antibacterial Dental Composites With Chlorhexidine and Mesoporous Silica, "Journal of Dental Research, 2014, Vo. 93(12), pp. 1283-1289.
Anacker, E. W., "Light Scattering by Cetylpyridinium Chloride Solutions", The Journal of Physical Chemistry 62, 41-45, doi:10.1021/j150559a011 (1958).
Angelos et al., "Mesoporous silicate materials as substrates for molecular machines and drug delivery", Chemical Entineering Journal vol. 137, pp. 4-13, Mar. 15, 2008.
Asker, D., et al., "Formation and stabilization of antimicrobial delivery systems based on electrostatic complexes of cationic-nonionic mixed micelles and anionic polysaccharides" Journal of agricultural and food chemistry 59, 1041-1049, doi:10.1021/jf103073w (2011).
Bourbia, M et al., "Cariogenic Bacteria Degrade Dental Resin Composites and Adhesives", J Dent Res 92 (11):989-994, 2013.
Cai, S., et al., "Effects of subinhibitory concentrations of chemical agents on hydrophobicity and in vitro adherence of *Streptococcus mutans* and *Streptococcus sanguis*", Caries research 28, 335-341, doi: 10.1159/000261998 (1994).
Canadian Patent Application No. 3,023,455, Office Action dated Apr. 1, 2022.
Canadian Patent Application No. 3,023,455, Office Action dated Feb. 21, 2020.
Canadian Patent Application No. 3,023,455, Office Action dated Jul. 12, 2023.
Canadian Patent Application No. 3,023,455, Office Action dated May 24, 2019.
Canadian Patent Application No. 3,023,455, Office Action dated Sep. 26, 2019.
Canadian Patent Application No. 3,023,455, Office Action dated Sep. 5, 2023.
Connor, E. E., et al., "Gold nanoparticles are taken up by human cells but do not cause acute cytotoxicity", Small 1, 325-327, doi:10.1002/smll.200400093 (2005).
Cortesi, R., "Effect of cationic liposome composition on in vitro cytotoxicity and protective effect on carried DNA", International Journal of Pharmaceutics 139, 69-78, doi: 10.1016/0378-5173(96)04574-7 (1996).
De Paula, G. F., et al., "Physical and Chemical Characterization of Poly(hexamethylene biguanide) Hydrochloride" Polymers 3, 928-941, doi:10.3390/polym3020928 (2011).
European Patent Application No. 17798447.3, Extended European Search Report dated May 22, 2019.
European Patent Application No. 17798447.3, Office Action dated Sep. 30, 2021.
Finer, Y., et al., "Influence of silanated filler content on the biodegradation of bisGMA/TEGDMA dental composite resins", Journal of Biomedical Materials Research Part A, 75-84, doi:10.1002/jbm.a (2007).
Finer, Y., et al., "Salivary esterase activity and its association with the biodegradation of dental composites", Journal of dental research 83, 22-26 (2004).
Finer, Y., et al., "The influence of resin chemistry on a dental composite's biodegradation", Journal of biomedical materials research. Part A 69, 233-246, doi: 10.1002/jbm.a.30000 (2004).
Haps, S., et al., "The effect of cetylpyridinium chloride-containing mouth rinses as adjuncts to toothbrushing on plaque and parameters of gingival inflammation: a systematic review", International Journal of Dental Hygiene 6, 290-303, doi:10.1111/j. 1601-5037.2008. 00344.x (2008).
Hatton, B. et al., "Past, Present, and Future of Periodic Mesoporous Organosilicas The PMOs", Accounts of chemical research 38, 305-312 (2005).
Hubner, N. O., et al., "Octenidine dihydrochloride, a modern antiseptic for skin, mucous membranes and wounds", Skin pharmacology and physiology 23, 244-258, doi:10.1159/000314699 (2010).
Huo, Q., et al., "Surfactant control of phases in the synthesis of mesoporous silica-based materials", Chemistry of Materials 4756, 1147-1160 (1996).
Imazato, S., et al., "Incorporation of bacterial inhibitor into resin composite", Journal of dental research 73, 1437-1443, doi:10.1177/00220345940730080701 (1994).
International Patent Application No. PCT/CA2017/050586, International Preliminary Report on Patentability dated Nov. 20, 2018.
Lu, J. et al., "Mesoporous silica nanoparticles as a delivery system for hydrophobic anticancer drugs" Small (Weinheim an der Bergstrasse, Germany) 3, 1341-1346, doi:10.1002/smll.200700005 (2007).
Ma, Q., et al., "Antimicrobial properties of lauric arginate alone or in combination with essential oils in tryptic soy broth and 2% reduced fat milk", International Journal of Food Microbiology 166, 77-84, doi:10.1016/j.ijfoodmicro.2013.06.017 (2013).
Martinez, V., et al., "Evaluation of eye and skin irritation of arginine-derivative surfactants using different in vitro endpoints as alternatives to the in vivo assays", Toxicology Letters 164, 259-267, doi:10.1016/j.toxlet.2006.01.005 (2006).

(56) References Cited

OTHER PUBLICATIONS

Mirska, D. et al., "Biophysical and biochemical properties of a binary lipid mixture for DNA transfection", Colloids and Surfaces B: Biointerfaces 40, 51-59, doi:10.1016/j.colsurfb.2004.10.007 (2005).

Nicoletti, G., et al., "The antimicrobial activity in vitro of chlorhexidine, a mixture of isothiazolinones ('Kathon' CG) and cetyl trimethyl ammonium bromide (CTAB)", Journal of Hospital Infection 23, 87-111, doi:10.1016/0195-6701(93) 90014-Q (1993).

Nooney, R. I. et al., "Synthesis of nanoscale mesoporous silica spheres with controlled particle size" Chemistry of Materials, 4721-4728 (2002).

Pinnaduwage, P., et al., "Use of a quaternary ammonium detergent in liposome mediated DNA transfection of mouse L-cells", BBA—Biomembranes 985, 33-37, doi:10.1016/0005-2736(89)90099-0 (1989).

Pitten, F. A. et al., "Antimicrobial efficacy of antiseptic mouthrinse solutions", European journal of clinical pharmacology 55, 95-100 (1999).

Rohrer, N. et al., "Antimicrobial efficacy of 3 oral antiseptics containing octenidine, polyhexamethylene biguanide, or Citroxx: can chlorhexidine be replaced?" Infection control and hospital epidemiology: the official journal of the Society of Hospital Epidemiologists of America 31, 733-739, doi:10.1086/653822 (2010).

Takahashi, H. et al., "Modification of gold nanorods using phosphatidylcholine to reduce cytotoxicity", Langmuir 22, 2-5, doi:10.1021/la0520029 (2006).

U.S. Appl. No. 17/464,211, Office Action dated Aug. 1, 2023.

Van Landuyt, K. L. et al., "Systematic review of the chemical composition of contemporary dental adhesives", Biomaterials 28, 3757-3785, doi:10.1016/j.biomaterials.2007.04.044 (2007).

Verraedt, E., et al., "Controlled release of chlorhexidine from amorphous microporous silica", Journal of controlled release: official journal of the Controlled Release Society 142, 47-52, doi:10.1016/j.jconrel.2009.09.022 (2010).

Wei et al., "Synthesis of polymer—Mesoporous Silica Nanocomposites", Materials, vol. 3, pp. 4066-4079, 2010.

Wei, D. et al., "Structural characterization and antibacterial activity of oligoguanidine (polyhexamethylene guanidine hydrochloride)" Materials Science and Engineering: C 29, 1776-1780, doi:10.1016/j.msec.2009.02.005 (2009).

Welk, A. et al. "The effect of a polyhexamethylene biguanide mouthrinse compared with a triclosan rinse and a chlorhexidine rinse on bacterial counts and 4-day plaque re-growth" Journal of clinical periodontology 32, 499-505, doi:10.1111/j.1600-051X.2005.00702.x (2005).

U.S. Appl. No. 17/464,211, Office Action dated Feb. 14, 2024.

U.S. Appl. No. 17/464,211, Office Action dated Oct. 19, 2024.

Xu, Xiaoming et al., "Formulation and characterization of a novel fluoride-releasing dental composite," Dental Materials 22 (2006) 1014-1023.

* cited by examiner

HIGHLY LOADED METAL OXIDE MATERIALS BY SELF-ASSEMBLY FOR EXTENDED BIOLOGICALLY ACTIVE MOLECULE RELEASE IN MEDICAL AND DENTAL APPLICATIONS

CROSS-REFERENCE TO RELATED APPLICATIONS

This application is a continuation of U.S. patent application Ser. No. 16/301,773, filed May 16, 2017, which is a National Stage Entry of International Application No. PCT/CA2017/050586, filed Nov. 15, 2018, which claims the benefit of U.S. Patent Application No. 62/337,016, filed May 16, 2016. U.S. patent application Ser. No. 16/301,773; International Application No. PCT/CA2017/050586 and U.S. Patent Application No. 62/337,016 are incorporated herein by reference.

STATEMENT OF GOVERNMENT SPONSORED SUPPORT

This invention was made with government support under R01 DE021385 awarded by the NIH. The government has certain rights in the invention.

FIELD

The present disclosure relates to the synthesis and use of biologically active agent-eluting mesoporous silica materials, and their application embedded in a biodegradable matrix for controlled release.

BACKGROUND

The treatment of dental caries (tooth decay or cavities) is a 30-billion dollar problem worldwide. This is partially due to the high rate of recurrent caries around dental resin composite restorations (fillings), caused by acid production from bacteria that has infiltrated into the degraded restoration-tooth interface, where a resin adhesive is applied. It is therefore desirable to integrate an antimicrobial agent within the restoration adhesive and/or restoration. However, past attempts at doing so by direct mixing of a drug into the resin composite forming the bulk of the restoration have resulted in rapid short-term release of the antimicrobial into the oral cavity and decreased strength of resin through the formation of voids. One potential approach to circumvent this issue is to integrate mesoporous silica nanoparticles (MSNs) that have an encapsulated antimicrobial agent instead.

Utilizing mesoporous silica, and other porous metal oxides in the form of a coating on the surface of medical and dental implants may be a useful vector for the delivery of antimicrobials, anti-inflammatories or growth factors and other active agents. In this case the porous coating may elute the desired substance directly at the point of action, avoiding the need for systemic administration. This is especially important for control of bacteria at an implant site, as normally a systemic antibiotic would be prescribed after surgery. This is undesirable as the reduction of antibiotic use is an important step to avoid cultivating bacterial resistance to antibiotics and other adverse effects, such as allergic reactions.

Traditionally, drug loading in MSN pores requires a surfactant template to form the periodic pores, followed by template removal, and subsequent drug loading. This traditional process results in low drug loading primarily along the surface of the particle, and a short-term release, which is unsuitable for applications such as antimicrobial use. Through this traditional multi-phase batch method of synthesis, the amount of drug captured internally in most materials is <10% by weight, and release occurs quickly (order of days).

These shortcomings of traditionally synthesized MSNs for the long-term storage and release of antimicrobial drug have been shown to affect its performance in the previously described application of recurrent caries prevention. Past research (Zhang et al 2014)[1] mixed chlorhexidine-loaded mesoporous silica into a commercial dental adhesive and studied the release of the chlorhexidine antiseptic drug and it's antimicrobial capabilities. Drug release in an uncontrolled manner stopped after approximately 10 days, and antimicrobial efficacy was only evaluated immediately post-synthesis. The short-term release seen is likely due to the fast dissolution of chlorhexidine from the surface of the loaded MSNs.

In the literature, some research groups have attempted to synthesize loaded MSNs through nontraditional methods, yielding mixed results.

One research group (Sanchez group, Fontecave et al 2013)[2] has published on "drug-templated mesoporous silica," however this group used model surfactant molecules in their synthesis to represent a drug, (e.g. those not in use as treatments) with a focus on bio surfactants. Pore channels within their MSNs were ill-formed, affecting the rate of release. Further, surfactant release in their final MSN products was primarily due to the degradation of particle silica structures, rather than a diffusion process, and as a consequence release was substantially completed within hours. Degradation release is additionally undesirable in MSNs for dental applications, as it may compromise the structural integrity of the adhesive, restorative material, or implant coating it is protecting.

Another group (He et al, 2010)[3] used the inherent toxicity of some surfactants to kill cancer cells, by producing conventional mesoporous silica materials, then allowing the templating surfactant to be released. They showed high loading and extended release, but were limited to molecules traditionally used to template these materials, rather than well understood and highly effective and biocompatible drugs. Additionally, the surfactant toxicity may also translate to human toxicity in other applications.

An additional study (Izquierdo-Barba et al. 2009)[4] encapsulated chlorhexidine (antiseptic drug) and an antimicrobial peptide in a surfactant micelle system, and condensed silica around the micelles, producing drug-loaded mesoporous silica in a one-step synthesis that showed release over 200 hours. However, the loading of antimicrobials was limited by the surfactant encapsulation efficiency, and was extremely low (<0.1% by weight).

SUMMARY

A biocompatible composite material for controlled release has been synthesized through a novel method of self-assembly. This material comprises a biocompatible metal oxide structure (an exemplary metal oxide being silica, $SiO_2$) with a loaded network of pores, filled substantially with a uniformly distributed biologically active micellizing amphiphilic molecule.

The material may be synthesized in both coating and particulate form (the particulate form herein referred to as mesoporous nanoparticles, or MSNs, with controllable diameters of about 300 nm to about 1.5 microns), with both forms comprising a semi-ordered network of pores, pore size ranging in a range from about 0.5 to about 100 nm in diameter.

This mesoporous metal oxide material contains a higher loading of active compound than possible through traditional diffusion-based loading methods (30% to 40% by weight compared to typical sub-10% internal loadings), and is further characterized in that when exposed to phosphate-buffered saline (PBS), the controlled release of the active amphiphilic molecule is predominantly diffusion-driven over time.

The amphiphilic molecule serves a dual role during the novel synthesis process, both providing a template for the formation of the porous metal oxide structure, and substantially loading said porous network with molecules having a biological activity as the desired final payload.

In the proposed applications the material would release antimicrobial from the surface of a dental implant and/or components such as abutment, or from a dental restorative adhesive in response to enzymatic degradation of the adhesive polymer matrix by bacteria and/or salivary enzymes. This would be to reduce post-implant-placement infection in the 2 weeks following surgery, or to address peri-implant disease/inflammation, or to reduce bacterial infiltration around dental restoration margins and/or surface, and reduce the occurrence of recurrent caries.

The present disclosure provides a biocompatible composite material for controlled release, comprising:

a biocompatible metal oxide structure containing a network of pores, said pores being filled with a micellizing, amphiphilic, biologically active agent distributed substantially uniformly throughout said network of pores in said metal oxide structure in self-assembled form, said composite material characterized in that when exposed to phosphate-buffered saline (PBS) the rate of controlled release of the amphiphilic biologically active agent is predominantly diffusion-driven over the rate of degradation of the metal oxide structure.

In an embodiment, a volume ratio of the micellizing amphiphilic biologically active agent to the biocompatible metal oxide may be above a first ratio for which the amount of the active agent is in sufficient amount for forming micelles at some point during the preparation of the composite material.

In another embodiment, this volume ratio of the amphiphilic biologically active agent to the biocompatible metal oxide may be between the first ratio and a second ratio of about 77% by volume.

In another embodiment, the ratio of the amphiphilic biologically active agent to the biocompatible metal oxide is between the first ratio and a second ratio of about 57% by volume.

In another embodiment, the ratio of the amphiphilic biologically active agent to the biocompatible metal oxide is between the first ratio and a second ratio of about 50% by volume.

The amphiphilic biologically active agent may be an active agent having a biocompatibility index greater than 1.

The amphiphilic, biologically active agent may be an antimicrobial agent, and the amphiphilic, biologically active agent may be any one of octenidine dihydrochloride, polyhexamethylene biguanide, cetylpyridinium chloride or lauric arginate.

The network of pores may comprise a network of interconnected pores. The pores may have a diameter size in range from about 0.5 to about 100 nanometers.

The composite material may be in a particulate form, with particles having a size in a range from about 50 to about 1000 nm in particle diameter.

Alternatively, the composite material may be formed as a coating.

The composite material may be characterized in that the controlled release of amphiphilic biologically active agent is not dependent on degradation of the biocompatible metal oxide structure.

The composite may be characterized in that during the course of the controlled release of the amphiphilic biologically active agent, the metal oxide structure maintains structural integrity.

The amphiphilic molecule serves a dual role of providing a template for the formation of the metal oxide structure comprising a network of pores, and substantially loading the porous network with said amphiphilic biologically active agent as a final payload.

The biocompatible metal oxide may be comprised of any of the following metal oxides: silicon dioxide, organosilicates, aluminosilicate, aluminum oxide, calcium phosphate, titanium dioxide, and zinc oxide.

The biocompatible metal oxide may be obtained with a species that react, condense, or assemble to form a biocompatible metal oxide.

The composite material may be incorporated into a polymer, a resin, or a resin composite. The polymer, resin, or resin composite comprises any one or combination of hydroxyethyl methacrylate, bisphenylglycidyl dimethacrylate, triethylene glycol dimethacrylate, other methacrylate-based and urethane-based polymers.

The composite material may be used as anyone or combination of, or as a component of, a coating for orthopedic implants, resin tooth bonding agent, cavity liner, cavity varnish, dental cement, resin coating or bulk of dentures, coating material or bulk of resin fillings, coating material for endosseous dental implant abutment or component, coating material for endosseous dental implant, resin composite tooth restorative material, denture relining, repairing, or rebasing resin, pit and fissure sealant and conditioner, temporary/interim/provisional crown and bridge resin, root canal (endodontic) filling resin sealer or endodontic core material, bone grafting material, coating material for total temporomandibular joint prosthesis, coating material for glenoid fossa prosthesis, coating material for mandibular condyle prosthesis, coating material for interarticular disc prosthesis, coating material for orthodontic appliance, resin bonding agent/cement for orthodontic brackets, coating material or bulk of orthodontic plastic bracket, oral cavity abrasive polishing agent, dentifrice, dental floss, and massaging pick or tip for oral hygiene.

The composite material may also be used to prevent or inhibit bacterial growth or bacterial proliferation.

The composite material may also be used to increase resistance of a material to enzymatic degradation and the micellizing amphiphilic biologically active agent is released from the composite material into a patient's body or patients oral cavity when the composite material is place in the patient's body or oral cavity.

The present disclosure provides a process for synthesizing a biocompatible composite material for controlled release, comprising:

a) a biocompatible metal oxide and a micellizing, amphiphilic, biologically active agent, mixed with a solvent to form a synthesis solution; and
b) at one point as the synthesis proceeds, said active agent self-assembles into a micellar system in the synthesis solution when a volume ratio of said active agent to a final loaded composite material is equal to, or above, a first ratio for which the amount of said active agent is in sufficient amount for self-assembly said metal oxide source to assemble around the solution-facing micelle walls, and form the composite material comprising a metal oxide structure condensed around loaded, self-assembled pores of said active agent to form the composite material.

The amphiphilic biologically active agent may be an active agent having a biocompatibility index greater than 1.

The amphiphilic, biologically active agent may be an antimicrobial agent, and may be octenidine dihydrochloride, polyhexamethylene biguanide, cetylpyridinium chloride or lauric arginate.

In an embodiment the composite material is characterized in that the volume ratio of said active agent to the final loaded composite material is equal or lower to a second ratio of about 77% by volume.

In another embodiment the composite material is characterized in that the volume ratio of said active agent to the final loaded composite material is equal or lower to a second ratio of about 57% by volume.

In yet another embodiment the composite material is characterized in that the volume ratio of said active agent to the final loaded composite material is equal or lower to a second ratio of about 50% by volume.

The composite material may be synthesized in particulate powder form by solution precipitation of the particles in said loaded and condensed metal oxide structure, and wherein the particulate powder have a size in a range from about 50 to about 1000 nm in particle diameter.

Alternatively, the composite material may be synthesized in a coating form by spreading a solution of solvent, said micellizing, amphiphilic, biologically active agent and biocompatible metal oxide source over a surface as a coating, where the evaporation of solvent forces an ordered co-assembly of the biologically active agent and metal oxide, with a subsequent increase in solution concentration by solvent evaporation causing the condensation of metal oxide around templating micelles into a porous solid coating.

In another embodiment, the composite material may be synthesized in a particulate form by aerosolizing or spraying a solution of solvent, the micellizing, amphiphilic, biologically active agent and biocompatible metal oxide source, where the evaporation of solvent from solution aerosol droplets forces an ordered co-assembly of the biologically active agent and metal oxide, with a subsequent increase in solution concentration by solvent evaporation causing the condensation of metal oxide around templating micelles into a porous solid coating.

The resulting composite material may be characterized by the network of pores comprising a network of interconnected pores.

The resulting composite material may be characterized by having pores having a diameter size in a range from about 0.5 to about 100 nanometers.

The resulting composite material may be characterized in that the controlled release of biologically active agent is not dependent on degradation of the biocompatible metal oxide structure.

The resulting composite material may be characterized in that during the course of the controlled release of the biologically active agent, the metal oxide structure maintains structural integrity.

The resulting composite material may be characterized in that the micellizing, amphiphilic, biologically active agent serves a dual role of providing a template for formation of the metal oxide structure comprising a network of pores, and substantially loading said porous network with the amphiphilic molecules as a final payload.

The biocompatible metal oxide may be comprised of any of the following metal oxides: silicon dioxide, organosilicates, aluminosilicate, titanium dioxide, and zinc oxide.

The biocompatible metal oxide may be obtained with a specie that react, condense, or assemble to form a biocompatible metal oxide.

The process may further comprise a step of incorporating the composite material into bio-compatible polymers. These bio-compatible polymers may comprise any one or combination of hydroxyethyl methacrylate, bisphenylglycidyl dimethacrylate, triethylene glycol dimethacrylate, other methacrylate-based and urethane-based polymers.

BRIEF DESCRIPTION OF THE FIGURES

Embodiments disclosed herein will be more fully understood from the following detailed description thereof taken in connection with the accompanying drawings, which form a part of this application, and in which:

FIG. 1 shows A) an 180 k magnification, 1 kV accelerating voltage scanning electron microscope (SEM) image of an MSN fully loaded with drug post synthesis; B) a 180 k magnification, 1 kV accelerating voltage SEM image of an MSN post drug release according to an embodiment.

FIG. 2 shows A) a transmission electron microscopy (TEM) image of the loaded MSNs captured at 300 kV accelerating voltage; B) an energy dispersive X-ray (EDX) mapping image of the loaded MSNs captured at 300 kV accelerating voltage. Nitrogen, the identifying atom in the drug octenidine (OCT), is shown in white; and C) another EDX mapping image of the loaded MSNs captured at 300 kV accelerating voltage. Silicon, (present in silica) is shown in white according to an embodiment.

FIG. 3 shows a TEM micrograph clearly indicating visible porous structure in the central particle. Scale bar is 50 nm according to an embodiment.

FIG. 4 shows a pore size analysis using density functional theory, with pore center to pore center d-spacing shown as the blue line. The broad pore diameter corresponds with the broad d-spacing seen by X-ray diffraction (XRD) according to an embodiment.

FIG. 5 shows XRD results for silica particles synthesized with OCT drug present above and below its critical micelle concentration (CMC), above which a micelle structure forms in solution according to an embodiment.

FIG. 6 shows XRD results for porous silica coating with the drug OCT present above its critical micelle concentration (CMC), above which a micelle structure forms in solution as demonstrated by the peak present according to an embodiment.

FIG. 7 shows a 70 k magnification, 0.5 kV accelerating voltage SEM image of a fragment of mesoporous silica coating fragment according to an embodiment.

FIG. 8 shows a release of OCT from OCT-templated porous silica coating either 2 or 6 layers thick in PBS at 37.degree. C. according to an embodiment.

FIG. 9A shows proliferation of *S. mutans* biofilm across a silicon substrate under fluorescent microscopy.

FIG. 9B shows proliferation of *S. mutans* biofilm across a porous silica substrate with no antimicrobial drug present.

FIG. 9C shows dead *S. mutans* cells stained using a live/dead staining kit on an OCT-templated porous silica substrate under fluorescent microscopy.

FIG. 10A shows a simplified schematic representation of a traditional MSN synthesis procedure.

Figure 14:
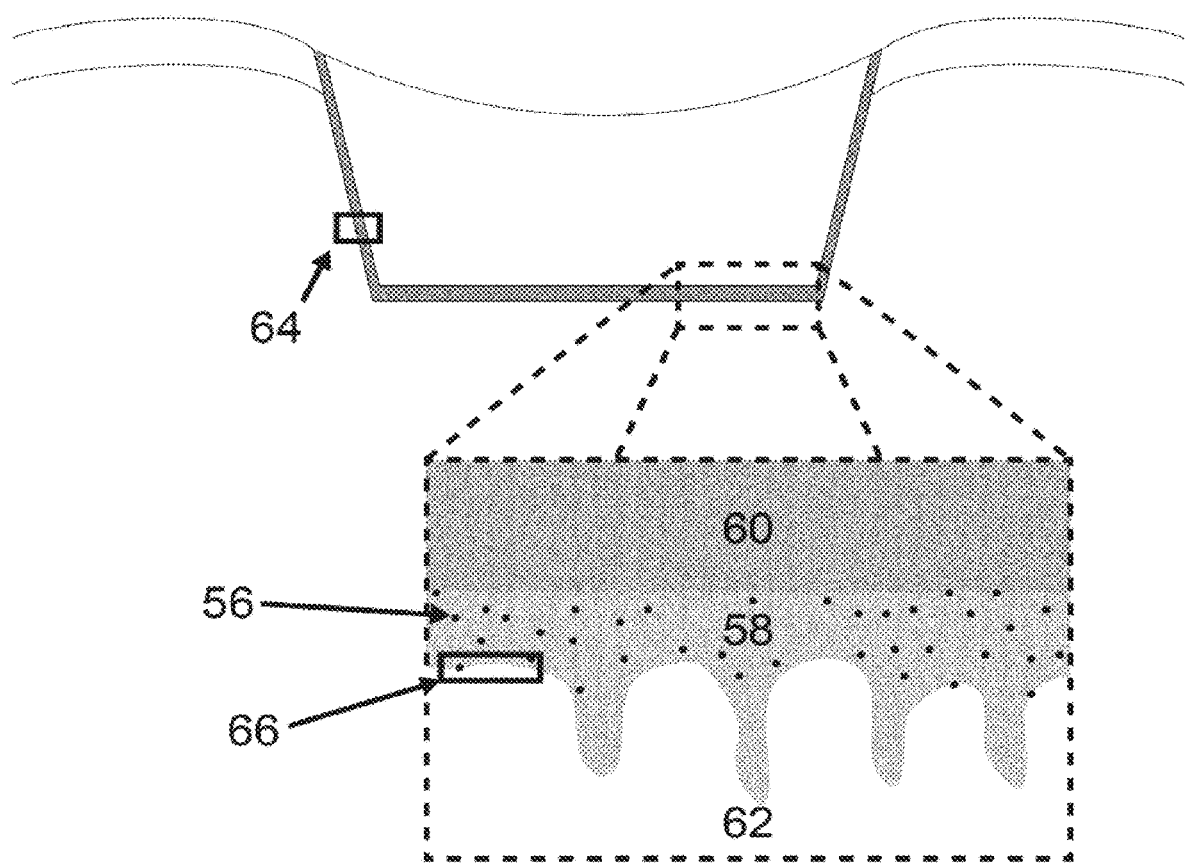

FIG. 14 shows a schematic showing the location in a dental restoration of the antimicrobial MSN-filled adhesive. The large structure is the tooth enamel surface over dentin, with a restoration in the center. The inset shows the composite-adhesive-dentin hybrid layer that is prone to enzymatic degradation and bacterial microleakage that may cause recurrent caries according to an embodiment.

Figure 15:
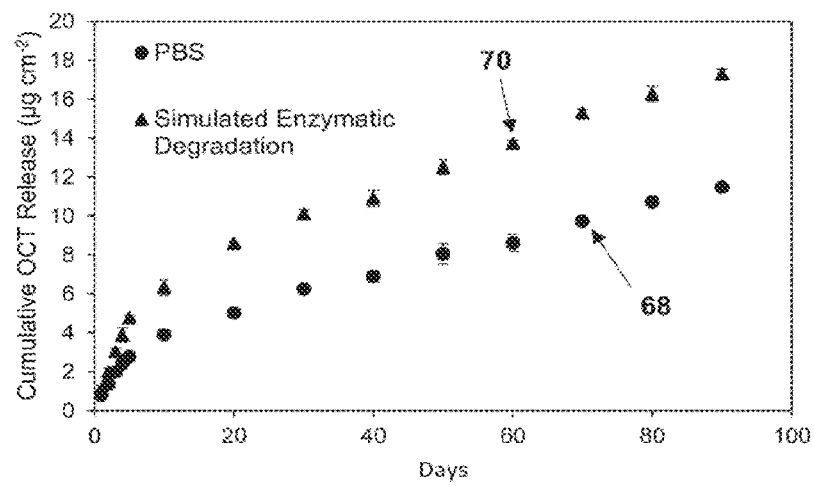

FIG. 15 shows long term release of antimicrobial drug OCT from a commercial dental adhesive loaded to 10% wt with OCT-templated MSNs according to an embodiment.

Figure 16:
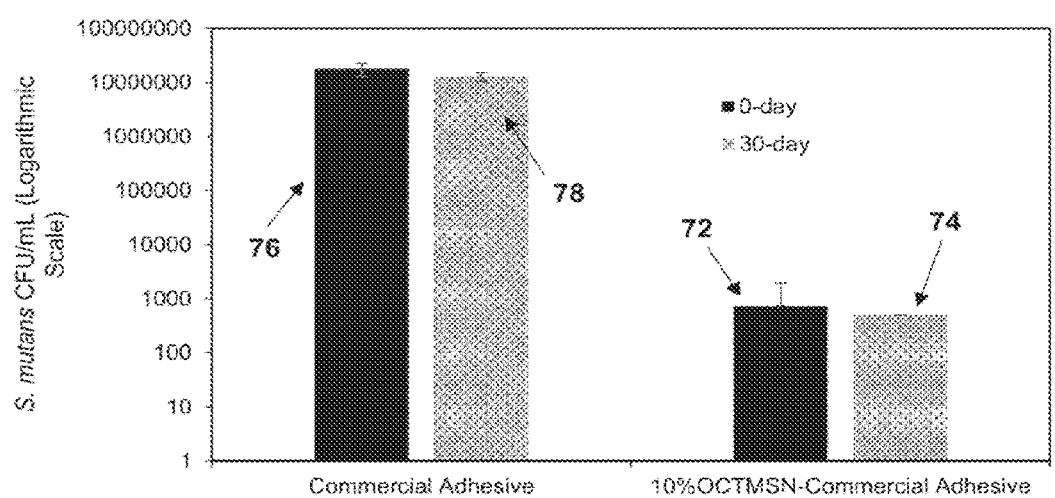

FIG. 16 shows the inhibition of *Streptococcus mutans* biofilm formation on commercial dental adhesive loaded to 10% wt with OCT-templated MSNs compared to the commercial adhesive alone, both immediately post-synthesis and after 30 days of drug pre-release according to an embodiment.

Figure 17:
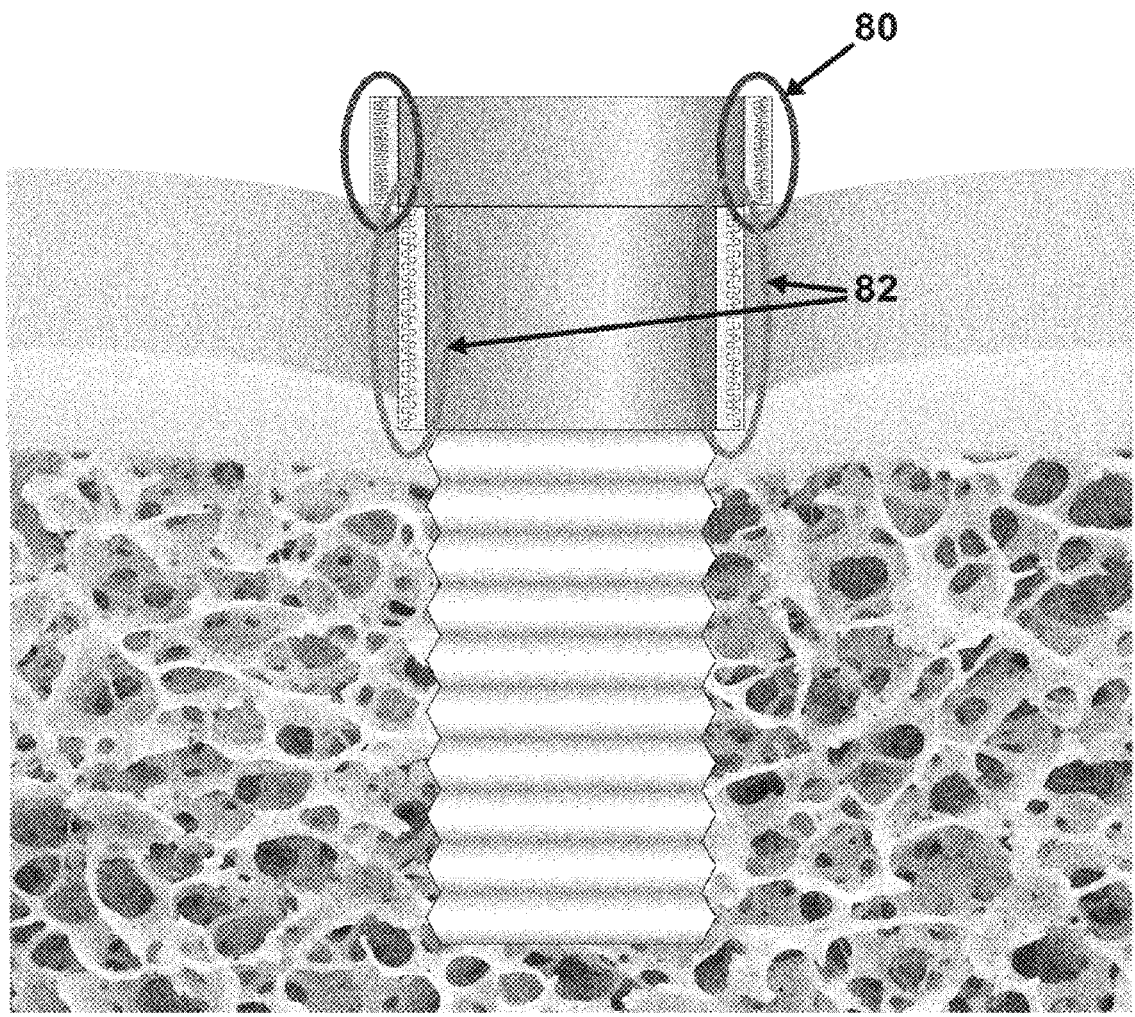

FIG. 17 is a model dental implant cross-section with a mesoporous silica coating according to an embodiment.

Figure 18:
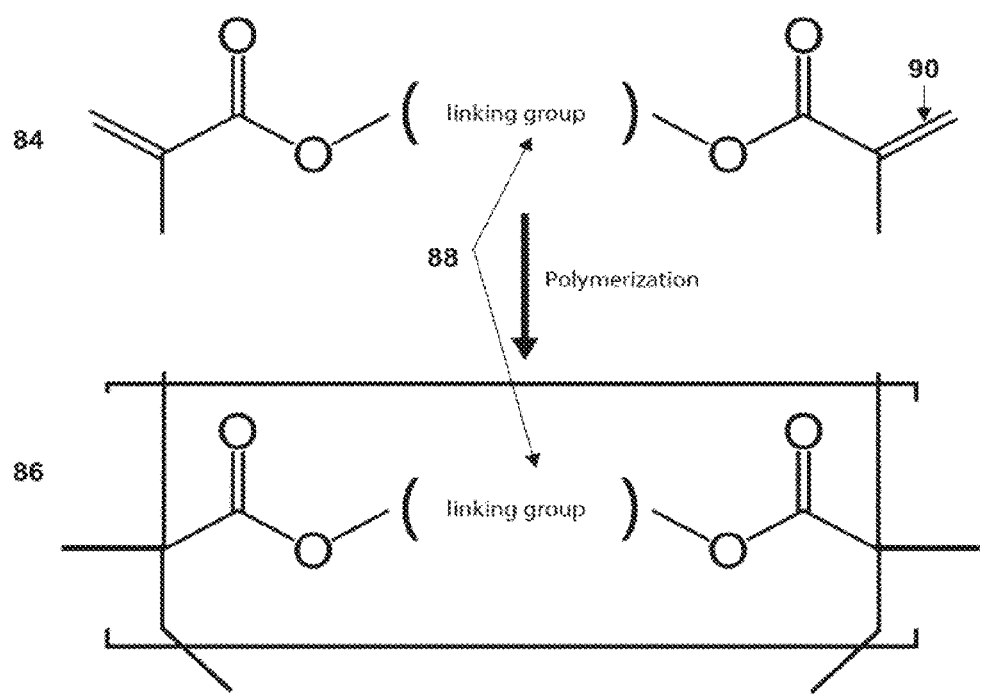

FIG. 18 shows the chemical structure of a generalized di-methacrylate monomer before and after polymerization according to an embodiment.

Figure 19:
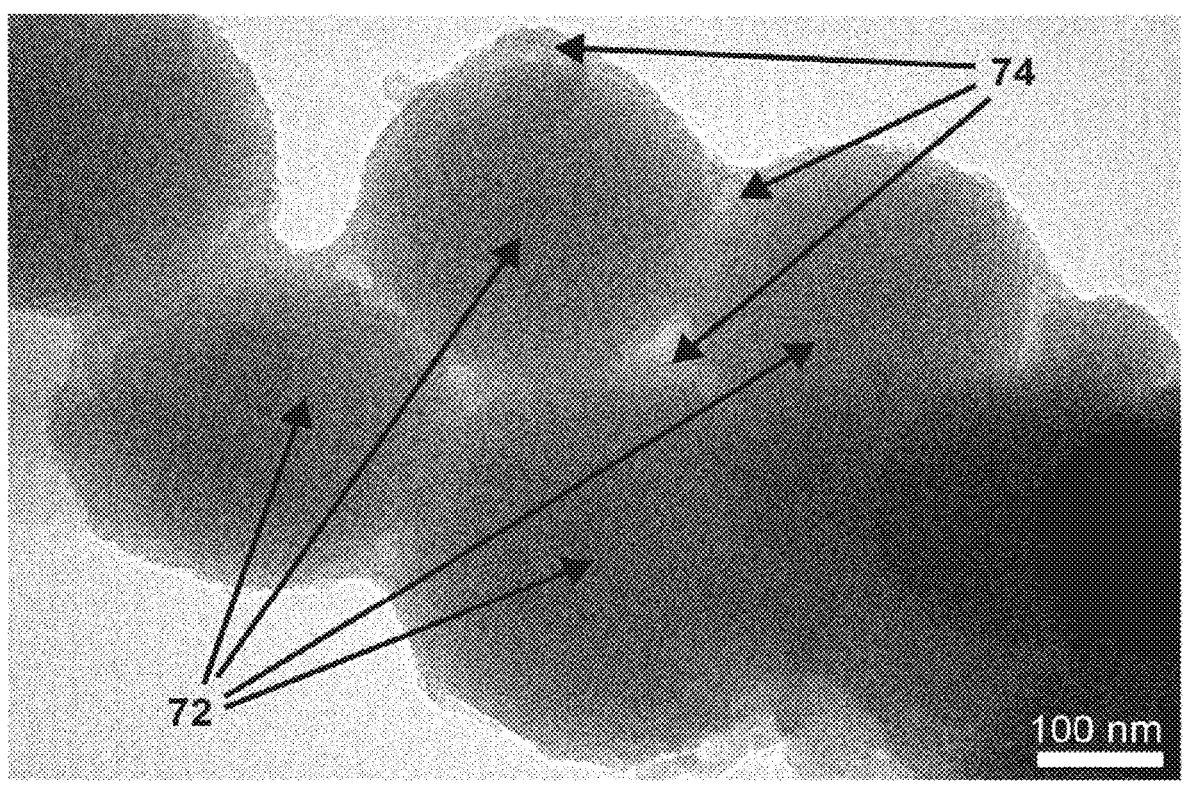

FIG. 19 shows OCT-templated MSNs that were subsequently functionalized with a covalently bound layer of fluorinated silane according to an embodiment.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms 'comprises' and 'comprising' are to be construed as being inclusive and open ended, and not exclusive. Specifically, when used in the specification and claims, the terms 'comprises' and 'comprising' and variations thereof mean the specified features, steps or components are included. These terms are not to be interpreted to exclude the presence of other features, steps or components.

As used herein, the term 'exemplary' means 'serving as an example, instance, or illustration,' and should not be construed as preferred or advantageous over other configurations disclosed herein.

As used herein, the terms 'about' and 'approximately' are meant to cover variations that may exist in the upper and lower limits of the ranges of values, such as variations in properties, parameters, and dimensions.

As used herein, the term 'micellizing' refers to the ability of a molecule in a particular solvent to form micelles above some critical micelle concentration (CMC).

As used herein, the phrases 'self-assembling', 'self-aggregating', and 'self-associating' refers to the movement of molecules from a dispersed unorganized random state into a desirable and controllable condensed state driven by intermolecular forces such as hydrophobic, hydrophilic and electrostatic interactions such as in the case of a micelle-forming amphiphilic molecule. Such controllable condensed state may be a micelle.

As used herein, the term 'amphiphilic' refers to the property of a molecule having at least two groups of differing solvent association preferences such as hydrophobic and hydrophilic groups, that may be characterized through the presence of a CMC in a particular solvent, above which the amphiphilic molecules micellize.

As used herein, the term 'intact' means maintaining structural integrity as one whole object or particle able to withstand physical forces to the same degree as before the described change.

As used herein, the term 'degradation' means the coming apart of an object, particle or molecule to two or more components while under physical, chemical or biological stress resulting in a loss of structure, physical strength, or function.

As used herein, the term 'biocompatible' refers to the property of a material or molecule of not causing harm to healthy and desirable living tissue or disrupting healthy and desirable biological processes during use of the material or molecule.

The term "biocompatibility index" is defined by the active agent's effective biological activity and its cytotoxic effect on human or animal cells. For example, when the biologically active agent is an antibacterial drug, the biocompatibility index may be defined by its antimicrobial activity and cytotoxic effect on human cell. The biocompatibility index will take into account both the results of the in vitro cytotoxicity, i.e., the concentration at which 50% of the murine fibroblasts are damaged, and the microbial effect, i.e., the concentration at which the baseline burden of the test microorganisms (e.g., *Escherichia coli* and *Staphylococcus aureus*) is reduced by at least 3 log 10 (99.9%). A biocompatibility index greater than 1 represent an antibacterial substance with an effective microbicidal activity combined with a relatively low cytotoxicity. For example, OCT, LAE and PHMB have a biocompatibility index of 2.11, 5.33 and 1.36 respectively. A biocompatibility index less than 1 indicates an antimicrobial agent with a relatively high cytotoxicity in a defined medium. For example, benzalkonium chloride, which is a common cationic surfactant, has been reported to have a biocompatibility index of 0.79. Cetyltrimethylammonium bromide (and other salts), the most popular pore-templating agent for mesoporous materials that shows biological activity, has a biocompatibility index of less than 0.125 suggesting extreme toxicity to mammalian cells.

As used herein, the terms 'biologically active agent', 'biological agent', or 'agent', refers to any synthetic, natural or derived compound having properties for treating or preventing a disease or illness, including: pharmaceutical drugs, pharmaceutical conjugated drugs, pharmaceutical prodrugs, antimicrobial or antiseptic agents, antifungal agents, peptides, DNA or any combinations thereof, which when introduced into the body causes a desired biological response.

As used herein the term 'metal oxide' refers to any material based primarily on a metal-oxide, metalloid-oxide, or organo-modified metal- or metalloid-oxide structures, including silicon dioxide, organosilicas with some unreacted organic groups or hydroxyl groups, organosilicas with bridging organic groups, titanium oxide, and aluminum oxide.

As used herein, the term 'metal oxide source' refers to any species that may react, condense, or assemble to form a desired metal oxide as defined above, such as organosilicates that hydrolize and condense to form silica or organosilica.

As used herein, the terms 'octenidine' and salts thereof, such as but not limited to 'octenidine dihydrochloride' refer to the antiseptic agent octenidine with the Chemical Abstracts Service number 0071251-02-0. Octenidine may be abbreviated to 'OCT'.

Metal Oxide Description and Properties

According to an embodiment, a self-assembled structure of amorphous metal oxide (as defined above, including silicon dioxide (silica), organosilicas with some unreacted organic groups or bridging organic groups, titanium oxide, and aluminum oxide) condensed around a network of templating micelles, such that the solid phase metal oxide contains pores with their entire volume filled by the micelle network. These micelles are formed by a biologically active agent having biological activity but also an amphiphilic micellizing behavior. In this way, the biologically active agent serves a dual role by providing a template for the formation of the metal oxide structure comprising a network of pores, and substantially loading the porous network with molecules having a biological activity as the desired final payload. The metal oxide framework can include some amount of unreacted (not fully condensed) hydroxyl groups, depending on its degree of condensation polymerization as a sol-gel or nanoparticle network.

The pores within the metal oxide structure are networked in such a way that they are accessible from the surface of the structure, and release of the biologically active agent from the pores in an appropriate solvent is not predicated on the alteration or destruction of the metal oxide structure. This represents an improvement over past assemblies of porous silica with a template amphiphilic biologically active agent that resulted in an imperfect network of pores, leading to the degradation of the silica structure as the agent was solvated and released.

According to an embodiment, the porous network may comprise a network of interconnected pores.

This metal oxide structure may take on many different forms and geometries according to the synthesis parameters and the specific biologically active agent used to form pores.

The size of metal oxide pores, described by their diameter, is directly related to the geometry of the templating micellizing amphiphilic biologically active agent and the micelles it forms. Typical relevant small molecules may form pores in metal oxide from 1 to 5 nm in diameter, as seen at 22 and 30.

However, larger agents may form self-assembled structures that result in pores where the smallest measurement may be over 100 nm. Pore size may be further controlled through the use of pore-swelling agents. These agents may affect the size of biologically active agent micelles during metal oxide condensation, and therefore the size of pores formed. Larger pores may release biologically active agent more quickly, and therefore the use of pore swelling agents may be desirable to control release rate.

Particulate Form

Figure 1:
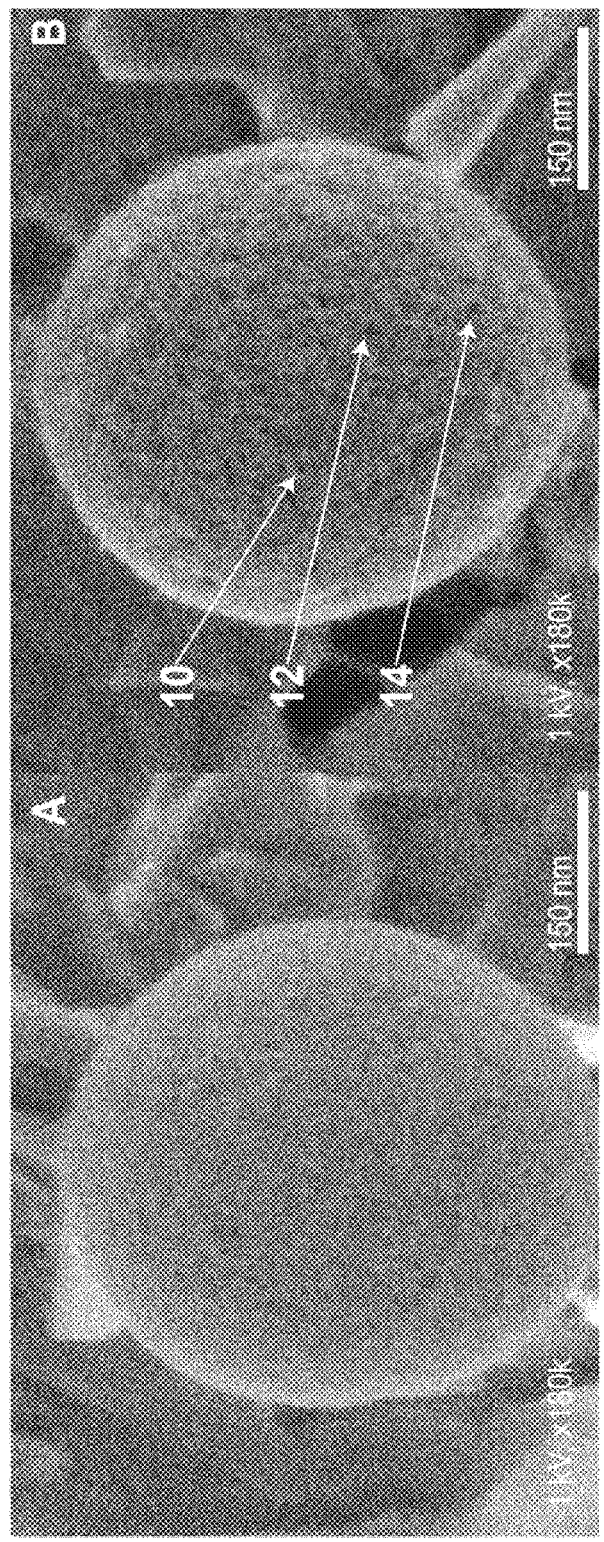
Figure 2:
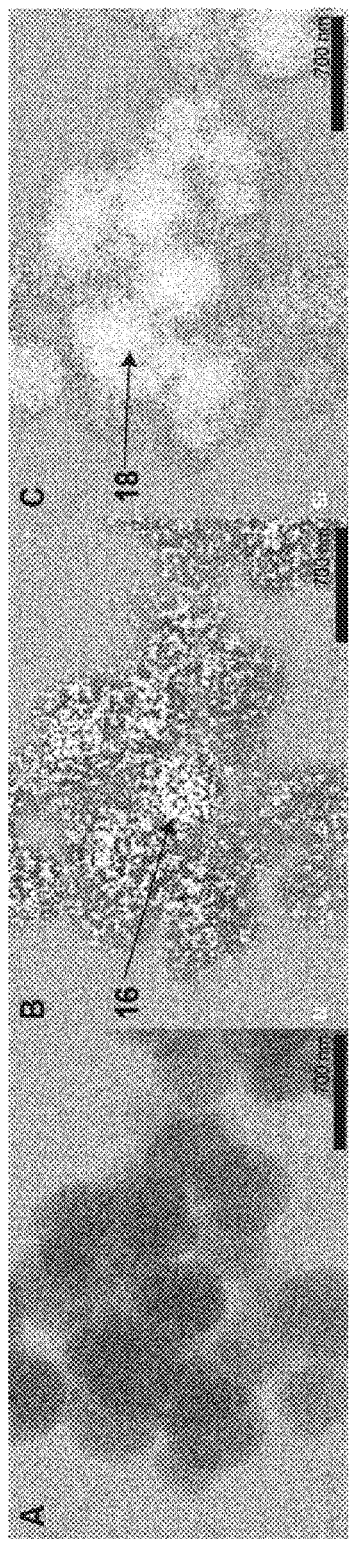
Figure 3:
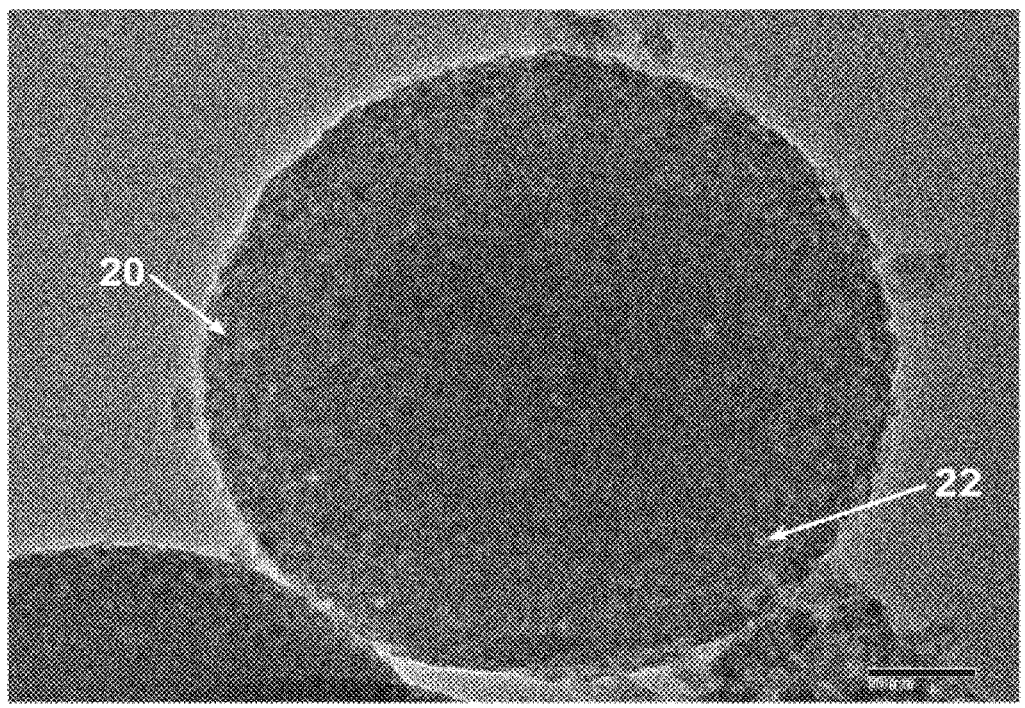

The biocompatible composite material may be synthesized in a particulate form by aerosolizing or spraying a solution of solvent along with the micellizing, amphiphilic, biologically active agent and the metal oxide source. Evaporation of solvent from solution aerosol droplets (drying) forces an ordered co-assembly of the biologically active agent and metal oxide, with a subsequent increase in solution concentration by solvent evaporation causing the condensation of metal oxide around templating micelles into a porous solid coating.

The biocompatible composite material may also be synthesized in a particulate form through precipitation from a solution of solvent along with the micellizing, amphiphilic, biologically active agent and the biocompatible metal oxide source including an organo-metal oxide precursor such as tetraethyl orthosilicate (TEOS) as a non-limiting example. This synthesis method requires the components to be in a high enough concentration such that self-assembly proceeds since the solvent volume may not change during the synthesis.

According to an embodiment, a self-assembled spherical MSN with its pore network substantially loaded with an amphiphilic biologically active molecule (for the examples described herein the exemplary amphiphilic molecule is the antimicrobial agent OCT) is shown in the SEM micrograph captured at 180 k magnification at 1 kV in FIG. 1A. After controlled drug release, empty pores on the surface of the MSN are visible in the 180 k magnification at 1 kV SEM micrograph FIG. 1B, as shown at marked positions 10, 12, and 14. These images demonstrate some drug loading obfuscating pore openings, but after drug removal these pores appear open and hollow, indicating that drug release may be from pores, and not primarily adsorbed material on the particle surface as in traditionally loaded particles. Drug release was sustained over a longer period of time (release over 8 days, versus 3 days for a traditionally-loaded MSN control), and at higher amounts than the traditional control (while still only releasing 34% of its total payload), showing promise for long term and high dosage antimicrobial applications. These images also show that during release, the drug diffused from the pores in silica, without needing the silica structure to degrade or decompose at all.

FIG. 2A shows a secondary electron image of the loaded particles at a magnification of 50 k and 300 kV accelerating voltage, where the EDX mapping in FIG. 2B highlights the location of amphiphilic molecules (in this example, OCT, identified by the presence of Nitrogen 16, in relation to the condensed metal oxide structure in MSNs (in this example, Silica, identified by the presence of silicon 18 in FIG. 2C). The generated Nitrogen and Silica signals match closely, and the results clearly show that the OCT molecules are mostly confined to MSNs, and are present in a consistent amount through the silica particles. They are also present in both the high- and low-contrast particles.

The TEM micrograph in FIG. 3 clearly indicates the visible porous structure of the particles, a metal oxide (silica) region in one of the particles indicated by 20, and a porous region of the same particle indicated at 22. An inter-pore spacing of approximately 2.72 nm was calculated from XRD data, corroborated by the internal porosity visualized in FIG. 3, as well as nitrogen adsorption porosity results. Pore diameter analysis through density functional theory from nitrogen adsorption data is shown in FIG. 4, yielding the value of 1.2 to 2 nm at point 24 and agreeing with the pore-pore d-spacing of 2.72 nm.

MSN porosity caused by the self-assembly of the exemplary molecule, OCT dihydrochloride, in micelles was demonstrated with XRD as shown in FIG. 5. Absence of XRD peak (26) is consistent with samples containing too little OCT to template pores, while a low, broad XRD peak (shown at 28) is consistent with a disordered mesoporous structure, where pores are not necessarily aligned, but demonstrate an average periodicity (d-spacing). This d-spacing was approximately twice the pore width found by nitrogen adsorption, and agrees with a calculated 50% porosity by volume (and therefore about 50% OCT by volume) and microscopy observations in FIGS. 1, 2, and 3.

Coating Form

The biocompatible composite material may be synthesized in a coating form by spreading a synthesis solution of solvent, micellizing amphiphilic biologically active agent, and biocompatible metal oxide source such as an organometal oxide precursor, over a surface as a coating. This spreading may be but is not limited to dip-coating, spin-coating or spray coating, the common element being that a surface covered by the synthesis solution. The evaporation of solvent forces an ordered co-assembly of the biologically active agent and metal oxide, with a subsequent increase in solution concentration by solvent evaporation causing the condensation of metal oxide around templating micelles into a porous solid coating.

In an embodiment the coating form may be but is not limited to a thickness of 100 nm to 1 mm in thickness and of any surface area. This form is characterized by a flat, smooth surface geometry over a longer line scale than the particulate form. The coating is comprised of the same porous silica structure with biologically active agent described previously. Coatings may also be layered over each other to add different biologically active agents or increase total biologically active agent and period of release. The coating may act as a coating over the surface of a substrate material, for example silicon, amorphous silica (glass), ceramic or titanium.

Figure 6:
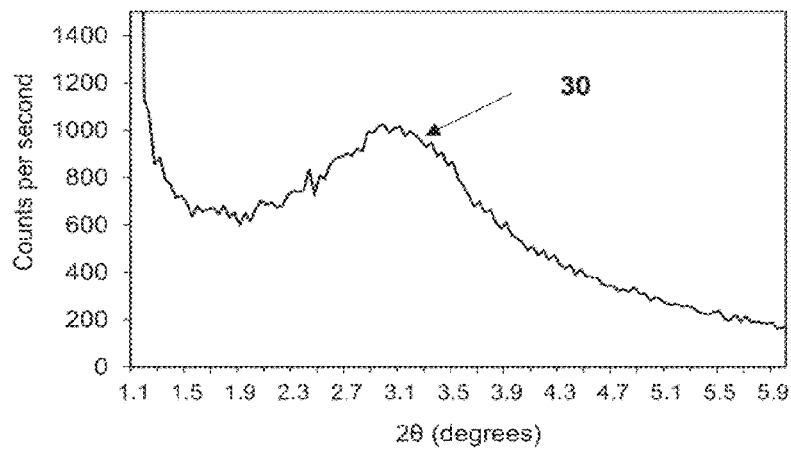

In analysis of exemplary coatings comprising of porous silica with OCT as the contained biologically active agent, XRD revealed the presence of a porous structure within silica identical to that seen in the particulate form, shown in FIG. 6 by the peak at 30. This pore structure also contained a 2.72 nm pore-pore d-spacing and characteristic broad peak indicating unaligned pore structure.

Figure 7:
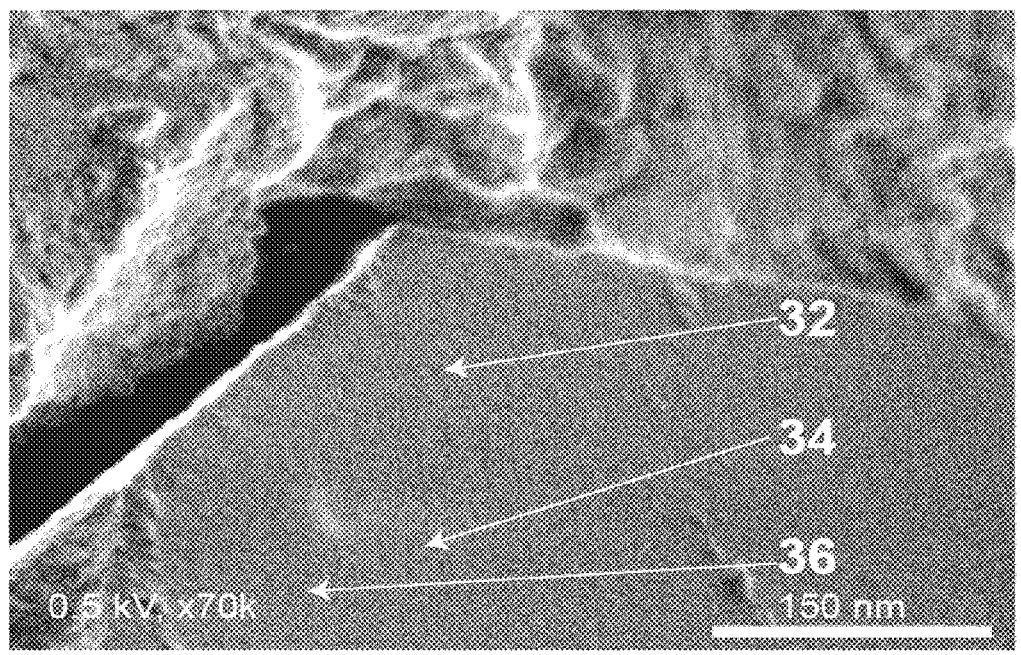

In SEM micrographs of the surface of the coating, such as the one shown in FIG. 7, pore openings are visible across the structure (at 32, 34 and 36), indicating the accessibility of the porous network from the exposed surface of the coating.

Figure 8:
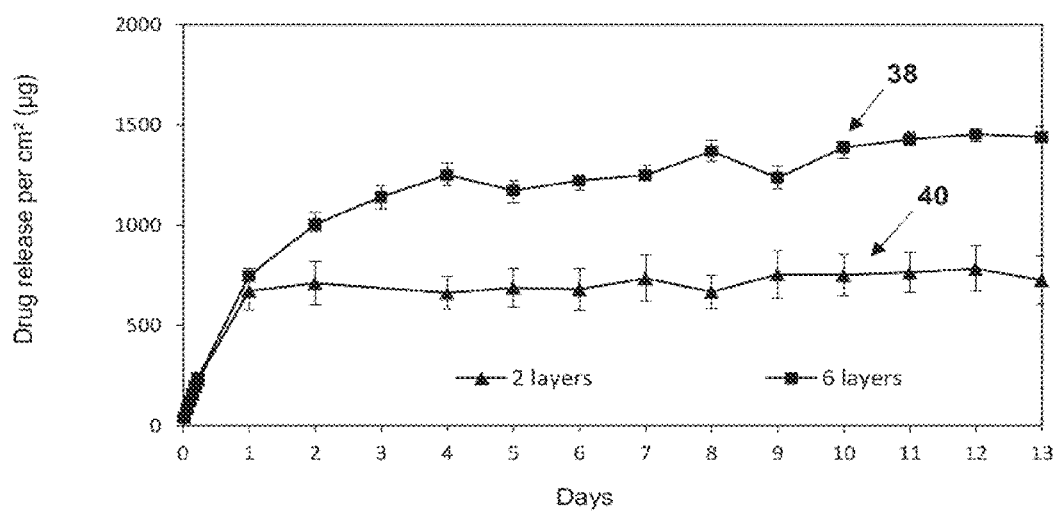

Release of OCT from the example silica coatings over a silicon substrate was monitored in PBS at 37° C. under gentle mixing, shown in FIG. 8. OCT release followed a similar kinetic profile as from the particulate form, however release completed much faster after 2 weeks for 6-layer samples (38), and only 2 days for 2-layer samples (40). This is due to differences in the coating thickness and mass, porous volume, and total OCT content of the multi-layer samples, and provides a simple method of control (coating thickness) for release kinetics.

Figure 9:
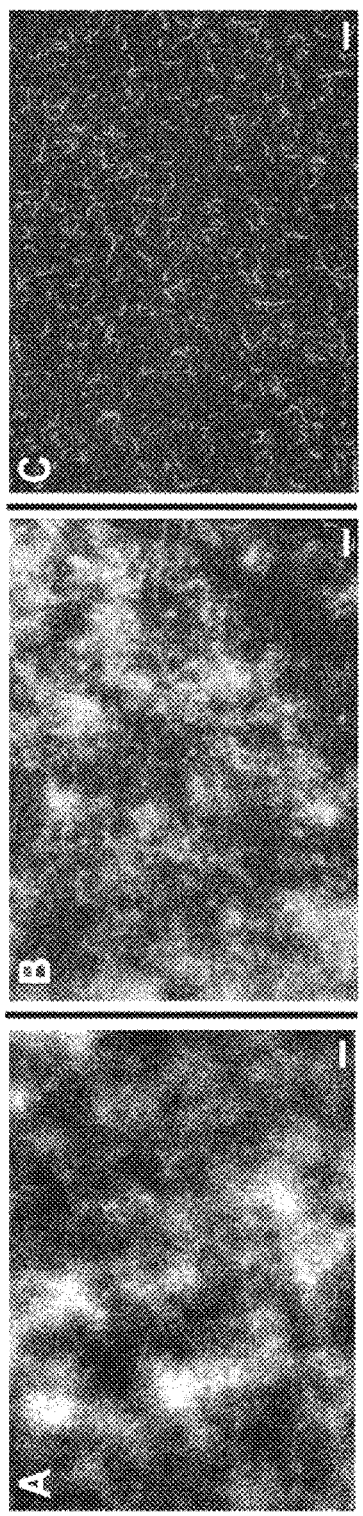

These coating samples containing OCT were extremely effective in preventing the formation of S. mutans biofilms over 24 hours when compared with a non-OCT containing porous silica coating in FIG. 9B, and the silicon substrate alone in FIG. 9A. The OCT-templated silica coatings showed complete inhibition of S. mutans colonization in FIG. 9C, with only dead cells identified on the surface.

Figure 10A:
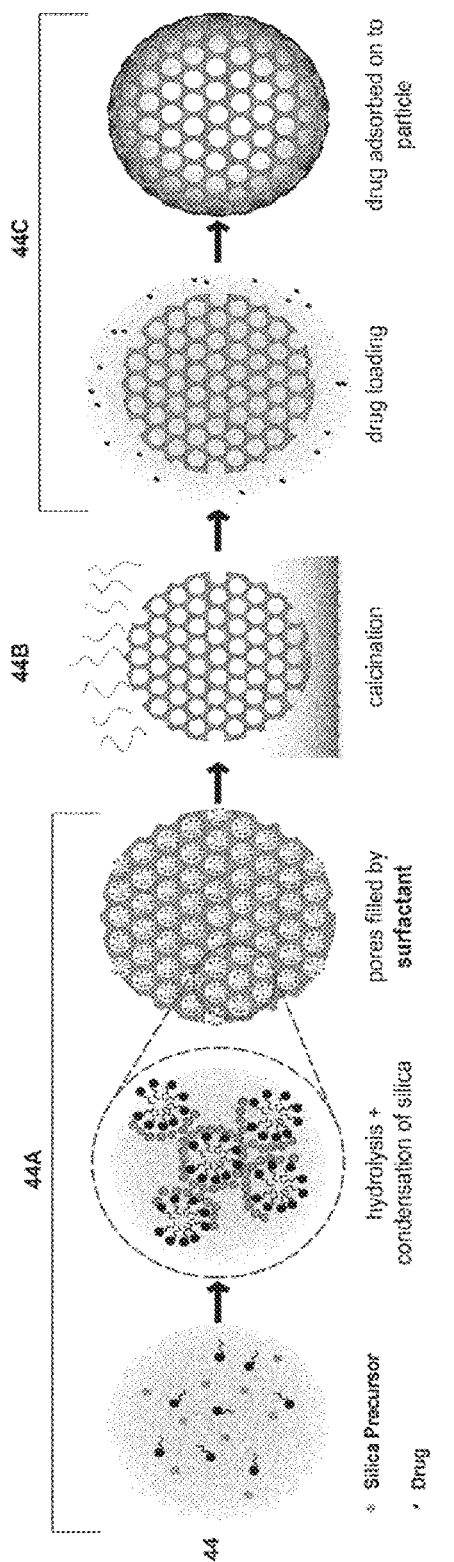
FIG. 10B shows the drug-templating approach according to an embodiment.
Figure 10B:
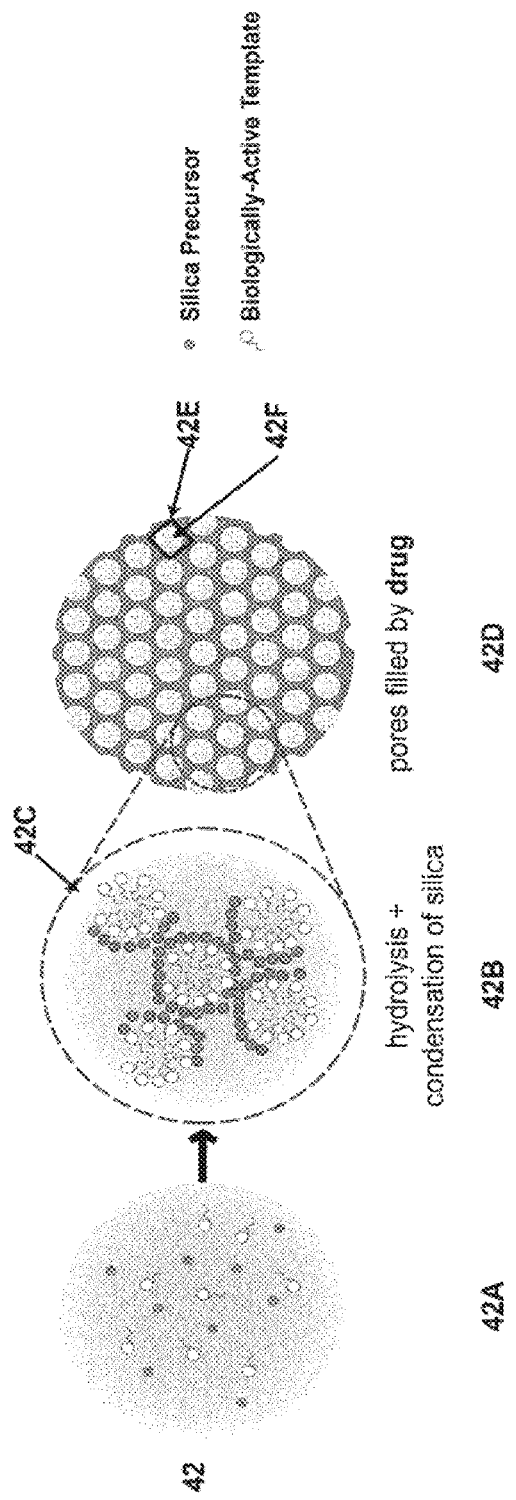
Figure 11:
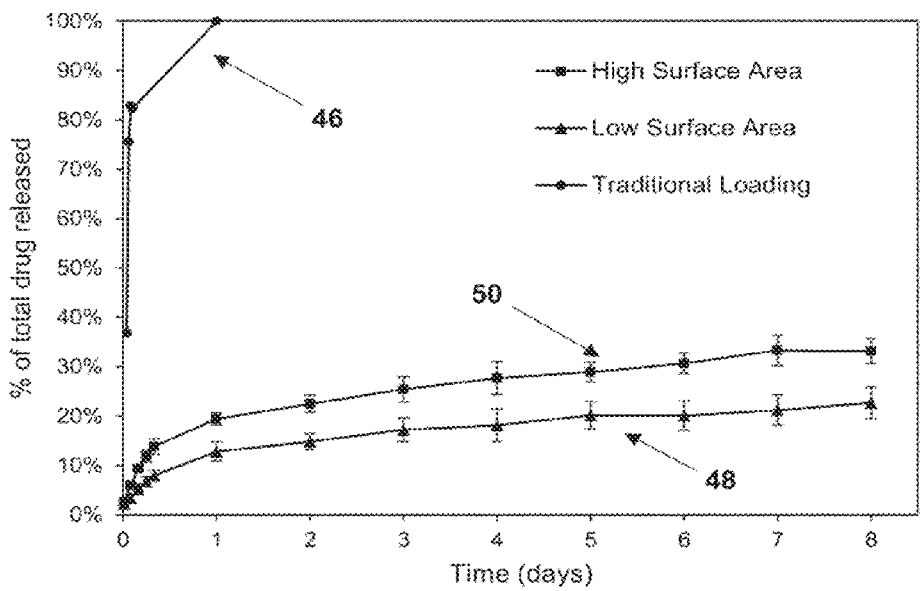
FIG. 11 shows a release of OCT from OCT-templated MSNs of two surface areas as well as traditionally loaded MSNs in PBS at 37.degree. C. according to an embodiment.
Figure 12:
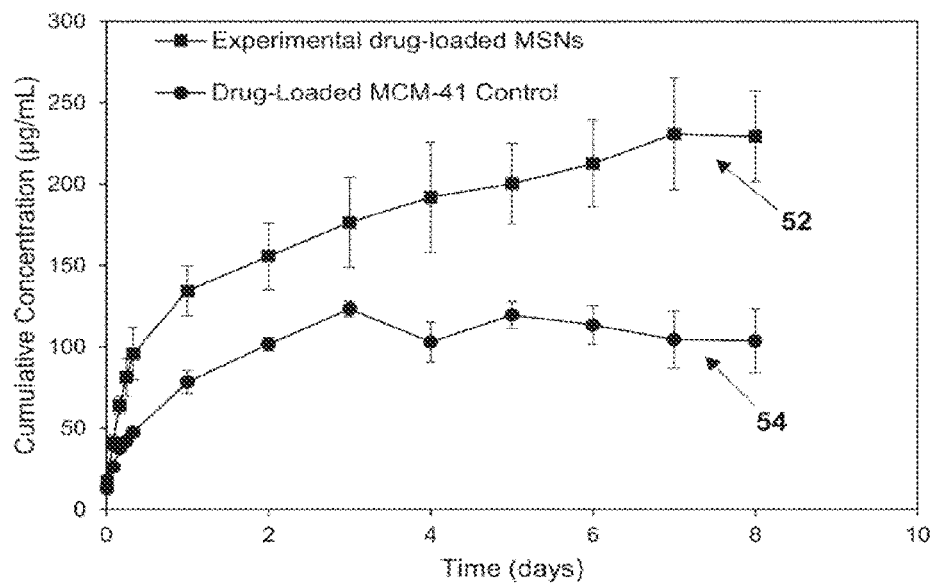
FIG. 12 shows cumulative drug release, as well as an incipient wetness-loaded MCM-41 MSN control according to an embodiment.
Figure 13:
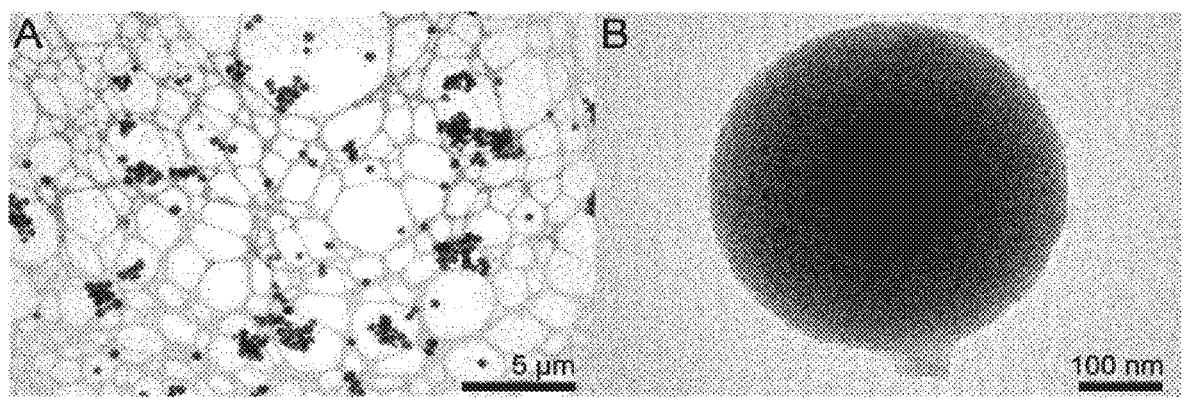
FIG. 13 shows OCT-templated MSNs that were incubated in PBS for 5 months post-drug release according to an embodiment.

Process Description for the Self-Assembly of Amphiphilic Molecules to Template Pores and Subsequent Condensation of Porous Material The simplicity of the presented novel synthesis procedure is contrasted with the traditional procedure for drug loading in FIG. 10B. According to an embodiment, the process 42 disclosed herein shows the present synthesis procedure for the particulate form. At step 42A a metal oxide precursor (e.g. silica pre-cursor tetraethyl orthosilicate) is mixed with a templating micellizing amphiphilic biologically active molecule (simply labeled 'drug' in the figure), such as OCT. This molecule performs as a dual agent, acting both as a micelle-forming amphiphilic molecule to template pores when present at a concentration above its CMC, while also inherently substantially loading the pore network with itself, a molecule having biological activity, e.g., antimicrobial activity. In step 42B the metal-oxide precursor undergoes hydrolysis within the synthesis solution, and condenses around the water-facing hydrophilic side of the micellar liquid crystals formed by the amphiphilic biologically active molecules in solution into, for example, silica (42C). This may occur when the synthesis solution components are at or above critical concentrations. This critical concentration may occur either immediately upon mixing the components (such as in a precipitation synthesis) or after some solvent evaporation has resulted in increasing the concentration of components (such as in the evaporative coating or aerosolizing/spray-drying process). Some metal oxide precursors, such as organosilanes to produce silica, may be reacted using an acid or base catalyst to increase the rate of metal oxide hydrolysis and condensation. Examples include hydrochloric acid, sodium hydroxide, and ammonia solutions. This reaction forms highly ordered periodic mesoporous structures (42D), whose pores (42E) follow the geometry and periodicity of the micelle (42F), the intermolecular forces holding these micelles together being non-covalent in nature.[5-8] The mechanics of self-assembly are similar whether the synthesis is through precipitation or through an evaporative coating or aerosolizing/spray-drying process.

The resulting structure is a highly porous metal oxide structure (e.g. silica) with a tightly packed load (e.g. a substantial quantity of the available pore volume is filled with the biologically active agent, such that in an embodiment, said quantity may be .about.100%) for controlled delivery of the biologically active agent.

The controlled release of the biologically active molecule from the metal oxide structure is characterized by a slow and sustained controlled release which is predominantly diffusion-driven out of the metal oxide structure rather than metal-oxide structure-degradation driven. According to an embodiment, the biologically active molecule may be released in a slow and sustained release manner through diffusion of the molecules from the open pores of the highly porous metal oxide structure, while not necessitating degradation of said metal oxide structure. The skilled person would understand that the controlled release is diffusion-driven when the rate of the diffusion of the molecule from the open pores is faster than the rate degradation of the metal oxide structure.

In the traditional '6-step' method of synthesis (44), shown in FIG. 10A, the metal oxide precursor is mixed and condensed with a surfactant intended for use as only a template (44A), followed by subsequent template removal through calcination (44B), and finally drug loading by diffusion and adsorption (44C). This process results in low loading and short-term release, properties which are unsuitable for applications such as antimicrobial use.[4,9]

By templating the pores of an MSN, coating, or other porous metal oxide structure, with an amphiphilic biologically active molecule, as proposed in this novel process, the complexity of synthesis may be greatly reduced, while simultaneously improving the volume % (and therefore weight %) of biologically-active agent loading and extending the release time of said molecule from the formed MSNs for dental and medical applications.

The improved loading weight % (about 34% of total particle weight is the biologically active agent OCT in a silica structure as determined by thermogravimetric analysis, equivalent to about 50% of particle volume or about 50% porosity) and extended release time are results of the formation of well-defined pore channels within the particle, substantially filled with biologically active agent, rather than having a small volume and weight % (<10%) adsorbed onto the outer-most pore walls at the surface of the structure, or poorly formed pore channels that degrade during release of the agent.

Evidence of slow, sustained drug release from particles synthesized by this novel process has been observed as shown in FIG. 11. OCT templated MSNs released only 35% of their drug contents over 8 days while freely mixed in phosphate buffered saline at 37.degree. C., while a % of total OCT released versus time plot 46 of traditionally OCT loaded control (at 40% weight OCT) released 100% of its contents in the first 24 hours of testing. Release also increased with increasing surface area (decreasing size), supporting the model of diffusion from a porous surface of fixed area. The plot 48 in FIG. 11 represents low surface area MSNs, and plot 50 high surface area MSNs, both synthesized with the novel process. While release increased with decreasing size, both particles synthesized through the novel process exhibited longer release times than the traditionally synthesized particle.

Cumulative OCT release of MSNs synthesized by the novel process is shown in FIG. 12 plot 52, as well as an OCT incipient wetness-loaded MCM-41 MSN control at FIG. 12 plot 54. These results corroborate those discussed from FIG. 11; the controlled particles cumulatively released less biologically active agent than the particles synthesized by the novel process.

As described above, a defining and required feature of the described material is the stability of the metal oxide structure. By maintaining a volume fraction of metal oxide structure in the composite above a certain point, the degradation of silica in PBS or similar biological conditions becomes negligible compared to the release of biologically active agent. If the metal oxide porous network is imperfect, insufficiently ordered, lacks access to the material exterior, or otherwise compromised, the metal oxide may degrade before or during biologically active agent release, and the structural integrity of the metal oxide may be compromised. The metal oxide structure shown in FIG. 3 has undergone total biologically active agent release but still maintains overall structure.

Furthermore, the metal oxide structures (OCT-templated mesoporous silica particles) in FIG. 13 were incubated in PBS for 5 months after biologically active agent release to simulate a biological environment, and do not demonstrate significant degradation, thus showing the enhanced stability of the well-ordered porous metal-oxide structure. This is in contrast with other "drug-templated" materials that show extensive degradation while drug is being released and limited hydrolytic stability due to their loosely packed drug-silica gel structure.

According to an embodiment, when exposed to PBS, the controlled release of the biologically active agent from the metal oxide structure may be characterized by a slow and sustained controlled release which is predominantly diffusion-driven rather than degradation driven. According to an embodiment, when exposed to PBS, the biologically active molecule may be released in a slow and sustained release manner through diffusion of the molecules from the open pores of the highly porous metal oxide structure, while not necessitating degradation of said metal oxide structure.

According to an embodiment, when exposed to PBS, the structure integrity of the highly porous metal oxide structure is maintained during the complete course of the controlled release of the biologically active agent.

According to an embodiment, when exposed to PBS, the controlled release of the biologically active molecule from the highly porous metal oxide structure is not dependent on degradation of the said structure.

According to an embodiment, the highly porous metal oxide structure may be considered as non-biodegradable when exposed to PBS.

Metal Oxide to Biologically Active Agent Ratio

The volume ratio between the pore templating biologically active agent and metal oxide in the final composite structure plays an important role in the stability of the structure by influencing the degree of porosity. The ratio is determined by the conditions of the synthesis of the material and by intrinsic properties of the biologically active agent.

The minimum volume ratio is limited by the critical micelle concentration of the biologically active agent (CMC). The CMC of biologically active agent is defined as the concentration of agent above which micelles form through micellization.

The desired structure containing a network of pores may be obtained when, at some point during the synthesis, the concentration of the biologically active agent becomes equal or above the agent's CMC. For example, the CMC for OCT is approximately 3.79 mM in water, while those of polyhexamethylene biguanide (PHMB), cetylpyridinium chloride (CPC), and lauric arginate (LAE) are 20-50 mM, 0.12 mM and 4.9 mM, respectively.

For example, when the structure is obtained by evaporative synthesis, solutions of biologically active agent and of metal oxide with a solvent are first mixed together. As evaporation of the solvent occurs, the concentration of agent increases and reaches or exceeds the CMC. Under such conditions, the biologically active molecules self-assemble as micelles, serving as the template for the network of pores. This evaporative process occurs for instance when the solution is spread over a surface to form a coating, or sprayed as an aerosol within each droplet to produce the particulate form.

Furthermore, the volume ratio of biologically active agent within pores to metal oxide is lower than an upper critical ratio. This volume ratio, and the density of the biologically active agent micelle, may determine the maximum weight percent of biologically active agent that the metal oxide material may accommodate. Above this upper critical ratio, the increase in porosity (pore volume as a fraction of total material volume) results in thinner and weaker metal oxide walls rendering the MSN structure susceptible to degradation. Eventually these walls are unable to support the structure of the metal oxide after the active agent is released from that area, and the structure collapses.

The synthesis of mesoporous materials with extremely high levels of porosity remains difficult due to the templating molecules micellizing nature, which limits the porosity to feasible structures. The highest levels of porosity for stable mesoporous silica is about 77% by volume, when the surfactant micelles are in a hexagonally close-packed arrangement and after heat treatment post-synthesis.[10] When the MSNs are prepared above this upper critical ratio (such as through evaporative process that force an assembly at higher template concentrations), the controlled release of the biologically active agent occurs rapidly and is predominantly driven by the degradation rate of the metal oxide structure. It is important to note that these limits are for biologically active agent within the metal oxide pores, and not condensed around the outside such as that in a more traditional preparation. This volume limit may directly affect the weight % limit, depending on the densities of both the biologically active agent and metal oxide structure used.

This is unsuitable for applications where it is desirable for the metal oxide structure to maintain its structural integrity such as when filling a void, providing structural integrity for a resin composite polymer system, or where the release of silica is undesirable such as in osseointegrated medical or dental implants.

According to an embodiment, the biologically active agent may be kept below 77% volume (which corresponds to for example 54 wt % for the drug OCT and the metal oxide structure silica). According to another embodiment, the biologically active agent may be kept below 57% by volume (which corresponds to for example 40 wt % for the drug OCT and the metal oxide structure silica). Alternatively, the biologically active agent is kept at a volume ratio value of 50% or less (which corresponds to for example 35 wt % or less for the drug OCT and the metal oxide structure silica) resulting in a stable metal oxide structure that may remain intact well beyond the timeframe of biologically active agent release.

Potential Amphiphilic Agent Molecules for Templating

According to an embodiment, the biologically active agent is a biologically active molecule having amphiphilic characteristics resulting in micellization when placed in aqueous conditions. The biologically active agent of the present invention is known primary for its biological activity and secondly for its surfactant characteristics. The amphiphilic biologically active agent of the present invention serves a dual role providing a template for the formation of the metal oxide structure comprising a network of pores, and substantially loading the porous network with molecules having a biological activity as the desired final payload.

According to an embodiment, biological active agent may be any amphiphilic biologically active agent that aggregates into a continuous micelle network. Biologically active agents shown to micellize via their amphiphilic properties include antimicrobial and antiseptic agents, tranquilizers, analgesics, peptide and non-peptide antibiotics, tricyclic antidepressants, antihistamines, anticholinergics, L-blockers, local anesthetics, non-steroidal anti-inflammatory drugs, and anticancer drugs. These compounds may organize into a continuous micelle network in order to template a network of pores, as opposed to a closed micelle system of a low number of molecules. This continuous micellar form exists under the conditions that allow metal oxide condensation (for example, with a silica source such as TEOS, above a pH of 10 or below a pH of 4, approximately).

According to an embodiment, the preferred amphiphilic biologically active agents are the amphiphilic antibacterial agents octenidine dihydrochloride (defined earlier), polyhexamethylene biguanide (PHMB), cetylpyridinium chloride (CPC), and lauric arginate (LAE). PHMB is a polymer antiseptic agent belonging to a family of polymer-based antiseptics called polyguanide oligomers.[11] PHMB has been shown effective at reducing populations and inhibiting growth of oral, gram positive and gram negative bacteria, and is sold commercially in some mouth rinses.[12,13] PHMB low molecular weight oligomers of approximately 6 units long may form micelles in solution, with a critical micelle concentration between 20 and 50 mM.[14]

Another promising alternative may be CPC, a quaternary ammonium surfactant and antiseptic with a CMC of 0.12 mM. Reported MICs of the compound are similar to CHX but may not possess the long-term plaque inhibiting effects of OCT and CHX and may stain teeth similarly to CHX.[15-18] CPC's greatest draw is its structural similarity to cetyltrimethylammonium chloride (a common mesoporous silica templating agent) and its strong ability to form micelles in solution.[19]

Another promising antimicrobial with strong micellization properties is lauric arginate (LAE), with a CMC of 4.9 mM.[20] LAE is food safe and has been tested against a wide variety of food-borne pathogens and shown to be effective. However, LAE may cause a bitter taste, and synthesis of MSNs would need to be modified as it may precipitate from solution at high pH.

According to an embodiment, the amphiphilic biologically active agent may be a synthetic, natural or derived compound having properties for treating or preventing a disease or illness, including: pharmaceutical drugs, pharmaceutical conjugated drugs, pharmaceutical prodrugs, antimicrobial or antiseptic agents, antifungal agents, peptides, DNA or any combinations thereof, which when introduced into the body causes a desired biological response. According to another embodiment, the amphiphilic biologically active agent may be an active agent with a suitable biocompatibility index. Such biologically active agent may have a biocompatibility index greater than 1. According to another embodiment, the preferred amphiphilic biologically active agent may be an antibacterial agent. According to a further embodiment, the most preferred amphiphilic biologically active agent may be the antibacterial agent OCT. OCT is an amphiphilic antiseptic agent with a biocompatibility index of greater than 1. OCT has shown a broad range of efficacy against gram positive and negative bacteria and is used currently as a mouth rinse, wound cleansing agent, topical antiseptic, and for other applications. The CMC of OCT was determined to be 3.79 mM. In antimicrobial studies we carried out, OCT compared favorably with CHX with respect to the common carious bacteria *S. mutans*, as well as a broad spectrum of other oral bacteria in previous studies, with no development of bacterial resistance.[12,21] Adverse effects of OCT as a mouth rinse are similar to those experienced during prolonged use of the common antimicrobial chlorhexidine. OCT's cytotoxicity is very similar to that of chlorhexidine, is not absorbed through mucous membranes.

Of interest is that OCT is a known cationic surfactant, which is why it was chosen as a candidate for tem plating pores in MSNs. The self-assembly and micellar properties of OCT in relation to templating mesoporous silica have not previously been studied.

Although some surfactants commonly used as pore templating agents, such as cetyltrimethylammonium bromide (CTAB), may be considered as having bioactive properties such as the ability to degrade and destroy bacterial cell walls, they remain largely unsuitable for use within the human body and are not considered as biologically active agent per se. This is because their bactericidal capabilities similarly make the molecule extremely cytotoxic and thus damaging to healthy human and animal tissue. CTAB is used in a number of nanoparticle synthesis processes and has been shown to be an undesirable and extremely cytotoxic impurity, able to reduce mammalian cell viability at concentrations of less than 1 μM, and thus impede the application of the synthesized materials as therapeutics[22-25]. CTAB and other and other purpose-designed surfactants and emulsifiers are known to have a biocompatibility index far lower than 1. Although the biocompatibility index of CTAB (by far the most popular pore-templating agent with antimicrobial activity) has not been reported directly, we may infer it from the results of two other studies: CTAB has an effective minimum inhibitory concentration (MIC) against *S. aureus* of 16 µg mL$^{-1}$ and a 50% reduction in murine fibroblasts at 2 µg mL$^{-1}$, therefore its biocompatibility index may be approximately 0.125, an extremely low value suggesting poor biocompatibility[28,27]. The toxicity of CTAB and these other purpose-designed surfactants and emulsifiers limit their applicability in pharmaceutical applications to emulsifiers at extremely low concentrations or as components in synthesis processes that are subsequently removed. By comparison, OCT and PHMB for example show high biocompatibility indices of 2.11 and 1.36 respectively[28]. The biocompatibility index of LAE hasn't been reported but may be determined through the same process as for CTAB: with an MIC of 11.8 µg mL$^{-1}$ against *E. coli* and a 50% reduction of human keratinocyte growth at 63 µg mL$^{-1}$ LAE's biocompatibility index is 5.33[29,30]. This allows these biologically active agents to be present within the porous material described here in high enough concentrations to act as an antimicrobial or effective agent as well as a pore templating agent without unacceptable cytotoxic effects.

Dental and Medical Applications of MSNs and Mesoporous Coatings

The immediate applications of interest are antimicrobial loaded MSNs for dental restorative composites and mesoporous coatings for medical or dental implant surfaces. However, this approach may be extended into any application of drug-eluting mesoporous biocompatible metal oxide structures where long-term release of a large amount of active material is required.

Physically robust MSNs may be used to encapsulate an antimicrobial agent within a polymer resin adhesive or bulk of a dental restoration for treatment of dental caries, as shown in FIG. 14. The antimicrobial MSNs are indicated at 56, the dental adhesive at 58, the bulk dental composite at 60, and the dentin of the tooth at 62.

The incorporation of antimicrobial-templated MSNs within resin adhesive may allow the adhesive to release antimicrobial to reduce bacterial load along the critical restoration-tooth interface at 64, through slow diffusion from the material surface and/or in response to bacterial and salivary enzymatic degradation of the critical resin-dentin interface at 66. As a secondary effect, the agent used may have other benefits such as the inhibition of salivary, bacterial, or tooth-dentin degradative enzymes, thus limiting the continued degradation of the restoration, the healthy tooth, and the bonded interface between the two. The use of the novel MSNs described here may stabilize drug within adhesive, and prolong release of drug upon exposure of MSNs to bacteria, while maintaining the adhesive's physical properties. (e.g. metal oxide structure may not degrade upon drug release with particles manufactured through the novel process, thus avoiding the formation of physically compromising voids).

FIG. 15 shows the slowed diffusive release of OCT from a polymerized commercial dental adhesive (3M ESPE Adper™ Scotchbond™ Multi-Purpose Adhesive being a non-limiting example) loaded with OCT-templated MSNs (10% wt within the adhesive) at 68, and the increased release in response to enzymatic biodegradation of the polymer matrix at 70, corresponding to only 0.6% wt of drug released in 90 days. FIG. 16 demonstrates the ability of the same material to inhibit growth of *S. mutans* biofilms (one of the primary etiological agents causing caries) upon synthesis at 72, and after 30 days of continuous release at 74 both results at the limit of detection since a statistically insignificant number of bacterial colonies were counted). This is compared to lack of any inhibition by the polymer adhesive on its own at both time points at 76 and 78 respectively. Fracture toughness specimens were produced by bonding human dentin to a commercial composite using either a commercial adhesive or the previously described OCT-MSN-adhesive and were tested for fracture toughness at 0, 30 and 180-day incubation in a simulated enzymatic biodegradative solution. The OCT-MSNs had no negative impact on the ability of the dental adhesive to bond to human tooth and maintain bond strength versus a significant reduction with the non-drug containing adhesive.

A cross section of another application of antimicrobial-templated mesoporous silica is shown in FIG. 17, in this case as a protective coating on a dental implant to avoid short-term post implant placement infection of soft tissue. The abutment sides are shown at 80, and the neck area is shown at 82. The bone-facing "screw" component would not have any coating, and thus interference with osseointegration is avoided.

Dental Polymers for Use in Adhesive Resin Composites

In order to facilitate the bonding of a dental restoration to exposed demineralized dentin, an adhesive system is commonly used. As illustrated in FIG. 14, there is opportunity for antimicrobial MSNs to be integrated into this adhesive resin, the system comprising one or more of several possible candidates for the polymeric resin. Since the OCT-MSN structure is stable under biologically relevant acidic conditions, this system may be an all-in-one material, or a two- of three-step primer and adhesive adhesives.

In a primer and adhesive system, a hydrophilic primer commonly containing the monomer hydroxyethyl methacrylate (HEMA) may be applied and allowed to infiltrate the exposed collagen fibril matrix of the dentin.

Then an adhesive may be applied frequently containing a cross-linking methacrylate monomer to provide structural strength and a diluent methacrylate monomer to allow the unpolymerized adhesive to flow more easily. Common monomers used in dentistry are, but not limited to, ═bis-GMA (bisphenylglycidyl dimethacrylate) (hydrophobic cross-linker), HEMA (2-hydroxyethyl methacrylate) (a hydrophylic monomer used to promote dentin wetting), and TEGDMA (triethylene glycol dimethacrylate) (added for flowability).[31] All are methacrylate monomers containing one or two ester bonds. These bonds are highly susceptible to cleavage by bacterial and salivary esterases.[32,33] This results in the release of bishydroxy propoxy phenyl propane (bisHPPP), methacrylic acid (MA), triethylene glycol (TEG) or the related mono-vinyl derivatives of TEGDMA and bisGMA, and ethylene glycol. The biodegradation of these polymers has been shown to expose embedded particles over time.[34]

The monomers described above are all methacrylate or di-methacrylate based and currently used in dentistry. The structure of a di-methacrylate monomer is shown in FIG. 18 at 84, with its polymerized form at 86. The linking group that changes between types of di-methacrylates (for example bisGMA and TEGDMA) is highlighted at 88, while the vinyl group necessary for polymerization is at 90. A number of other methacrylate and urethane based monomers exist that are also gaining popularity, and exhibit certain biodegradation properties with changing chemistries of the linking group or method of polymerization. Utilizing antimicrobial MSNs with these other monomers or mixtures of different monomers should not be ruled out. The skilled reader would understand that non-methacrylate monomers have been used in dentistry and may be suitable for the use of this invention.

By adjusting the chemical composition of this polymer system, the rate of biodegradation by bacterial and human salivary esterases may be controlled.[35] Incorporating biologically active agent-releasing MSN in this system minimizes agent release while particles are embedded in polymer, shown previously at 68, but allow for increased release in response to enzymatic degradation via esterase in a controlled manner, again shown previously at 70. These photocured esterase-containing polymer matrices and the loaded biologically active agent-nanoparticles may be used in other applications besides dental restoratives to provide controlled biodegradation, and subsequent agent release.

While the teachings described herein are in conjunction with various embodiments for illustrative purposes, it is not intended that these teachings be limited to such embodiments. On the contrary, the teachings described and illustrated herein encompass various alternatives, modifications, and equivalents, without departing from the embodiments, the general scope of which is defined in the appended claims.

Except to the extent necessary or inherent in the processes themselves, no particular order to steps or stages of methods or processes described in this disclosure is intended or implied. In many cases the order of process steps may be varied without changing the purpose, effect, or import of the methods described.

Modifications to the Metal Oxide Structure

According to an embodiment, the MSNs of the present invention may provide a ready scaffold upon which a shell may be added to provide a core-shell structure. The shell may comprise a single layer or more than one layer. Polymers, molecular machines, surface groups or even different forms of metal oxide may be used for the preparation of the shell.[8] These modifications may enhance stability of the metal oxide, extend release rate, may provide targeting for certain cells in biological systems, or even may act as gate molecules that 'open' only under certain stimuli, such as pH changes, or enzymatic activity.

Figure 4:
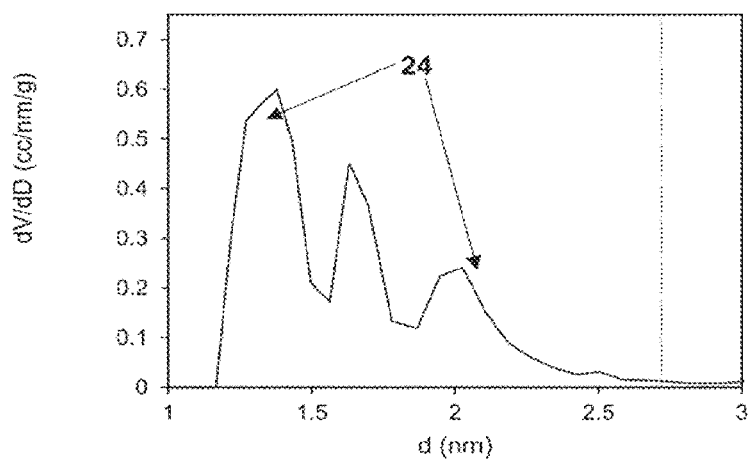
Figure 5:
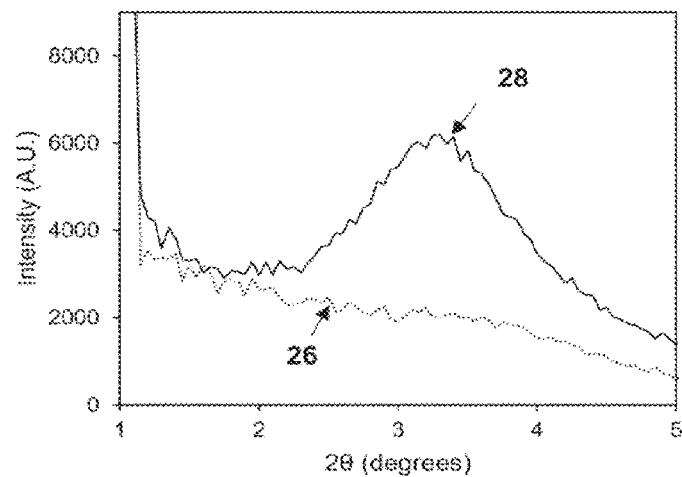

According to an embodiment, the open and accessible metal oxide surface of the MSN may act as a core for functionalization or growth of one or more porous metal oxide layers. These subsequent metal oxide layers may be identical, or may feature a different pore template, biologically active agent template, pore geometry, or a different metal oxide species. These modifications may allow for more control of the release rate of biologically active agent and the stability of the metal oxide structure. Such modifications are not possible for particles loaded with biologically active agent post synthesis via evaporation as seen in 44C due to the inaccessibility of metal oxide at the surface of the composite. In one example, OCT-templated mesoporous silica particles were synthesized as before, and before particle collection while OCT-MSNs were still suspended in the synthesis solution, but after TEOS reaction and particle self-assembly, a fluorinated silane was added to the solution and bound to the still-exposed silica on the outside of the particles as a shell. Unbound material was washed away after particle collection, leaving OCT-filled MSNs with a shell of fluorinated silane. Some of these particles are shown in FIG. 19 with the core particles at 72 and the silane shell at 74, appearing different from those particles in FIG. 4. This kind of direct functionalization of the outer metal oxide structure is not possible when there is a thick layer of adsorbed drug at the surface. Energy dispersive x-ray analysis of fluorinated silane-shell particles confirmed the presence of fluorine on the particles with a signal strength of about 10% compared to other elements (Si, O, C and N). No fluorine was detectable in particles synthesized without the fluorinated silane shell.

According to an embodiment, the composite material of the present invention may be used as anyone or combination of or as a component of a coating for orthopedic implants, resin tooth bonding agent, cavity liner, cavity varnish, dental cement, resin coating or bulk of dentures, coating material or bulk of resin fillings, coating material for endosseous dental implant abutment or component, coating material for endosseous dental implant, resin composite tooth restorative material, denture relining, repairing, or rebasing resin, pit and fissure sealant and conditioner, temporary/interim/provisional crown and bridge resin, root canal (endodontic) filling resin sealer or endodontic core material, bone grafting material, coating material for total temporomandibular joint prosthesis, coating material for glenoid fossa prosthesis, coating material for mandibular condyle prosthesis, coating material for interarticular disc prosthesis, coating material for orthodontic appliance, resin bonding agent/cement for orthodontic brackets, coating material or bulk of orthodontic plastic bracket, oral cavity abrasive polishing agent, dentifrice, dental floss, and massaging pick or tip for oral hygiene.

According to an embodiment, the composite material of the present invention may be used to prevent or inhibit bacterial growth or proliferation within a human or animal. Furthermore, the composite material may be used to prevent or inhibit bacterial growth or bacterial proliferation within the body or oral cavity of such human or animal.

According to an embodiment, the composite material of the present invention may be used to increase resistance of a material to enzymatic degradation. Furthermore, the micellizing amphiphilic biologically active agent may be released from the composite material.

The foregoing description of the preferred embodiments of the present disclosure have been presented to illustrate the principles of the invention and not to limit the invention to the particular embodiment illustrated. It is intended that the scope of the invention be defined by all of the embodiments encompassed within the following claims and their equivalents.

REFERENCES

1 Zhang, J. F. et al. Antibacterial Dental Composites with Chlorhexidine and Mesoporous Silica. Journal of Dental Research 93, 1283-1289, doi:10.1177/0022034514555143 (2014).

2 Fontecave, T., Boissiere, C., Baccile, N., Plou, F. J. & Sanchez, C. Using evaporation-induced self-assembly for the direct drug templating of therapeutic vectors with high loading fractions, tunable drug release, and controlled degradation. Chemistry of Materials 25, 4671-4678, doi: 10.1021/cm401807m (2013).

3 He, Q., Shi, J., Chen, F., Zhu, M. & Zhang, L. An anticancer drug delivery system based on surfactant-templated mesoporous silica nanoparticles. Biomaterials 31, 3335-3346, doi:10.1016/j.biomaterials.2010.01.015 (2010).

4 Izquierdo-Barba, I. et al. Incorporation of antimicrobial compounds in mesoporous silica film monolith. Biomaterials 30, 5729-5736, doi:10.1016/j.biomaterials.2009.07.003 (2009).
5 Lu, J., Liong, M., Zink, J. I. & Tamanoi, F. Mesoporous silica nanoparticles as a delivery system for hydrophobic anticancer drugs. Small (Weinheim an der Bergstrasse, Germany) 3, 1341-1346, doi:10.1002/sml1.200700005 (2007).
6 Nooney, R. I. & Thirunavukkarasu, D. Synthesis of nanoscale mesoporous silica spheres with controlled particle size. Chemistry of Materials, 4721-4728 (2002).
7 Hatton, B. & Landskron, K. Past, Present, and Future of Periodic Mesoporous Organosilicas The PMOs. Accounts of chemical research 38, 305-312 (2005).
8 Angelos, S., Liong, M., Choi, E. & Zink, J. I. Mesoporous silicate materials as substrates for molecular machines and drug delivery. Chemical Engineering Journal 137, 4-13, doi:10.1016/j.cej.2007.07.074 (2008).
9 Verraedt, E., Pendela, M., Adams, E., Hoogmartens, J. & Martens, J. A. Controlled release of chlorhexidine from amorphous microporous silica. Journal of controlled release: official journal of the Controlled Release Society 142, 47-52, doi:10.1016/j.jconrel.2009.09.022 (2010).
10 Huo, Q., Margolese, D. I. & Stucky, G. D. Surfactant control of phases in the synthesis of mesoporous silica-based materials. Chemistry of Materials 4756, 1147-1160 (1996).
11 Wei, D. et al. Structural characterization and antibacterial activity of oligoguanidine (polyhexamethylene guanidine hydrochloride). Materials Science and Engineering: C 29, 1776-1780, doi:10.1016/j.msec.2009.02.005 (2009).
12 Rohrer, N. et al. Antimicrobial efficacy of 3 oral antiseptics containing octenidine, polyhexamethylene biguanide, or Citroxx: can chlorhexidine be replaced? Infection control and hospital epidemiology: the official journal of the Society of Hospital Epidemiologists of America 31, 733-739, doi:10.1086/653822 (2010).
13 Welk, a. et al. The effect of a polyhexamethylene biguanide mouthrinse compared with a triclosan rinse and a chlorhexidine rinse on bacterial counts and 4-day plaque re-growth. Journal of clinical periodontology 32, 499-505, doi:10.1111/j.1600-051X.2005.00702.x (2005).
14 De Paula, G. F., Netto, G. I. & Mattoso, L. H. C. Physical and Chemical Characterization of Poly(hexamethylene biguanide) Hydrochloride. Polymers 3, 928-941, doi: 10.3390/polym3020928 (2011).
15 Cai, S., Simionato, M. R., Mayer, M. P., Novo, N. F. & Zelante, F. Effects of subinhibitory concentrations of chemical agents on hydrophobicity and in vitro adherence of *Streptococcus mutans* and *Streptococcus sanguis*. Caries research 28, 335-341, doi:10.1159/000261998 (1994).
16 Imazato, S., Torii, M., Tsuchitani, Y., McCabe, J. F. & Russell, R. R. Incorporation of bacterial inhibitor into resin composite. Journal of dental research 73, 1437-1443, doi:10.1177/00220345940730080701 (1994).
17 Pitten, F. a. & Kramer, a. Antimicrobial efficacy of antiseptic mouthrinse solutions. European journal of clinical pharmacology 55, 95-100 (1999).
18 Haps, S., Slot, D. E., Berchier, C. E. & Van der Weijden, G. A. The effect of cetylpyridinium chloride-containing mouth rinses as adjuncts to toothbrushing on plaque and parameters of gingival inflammation: a systematic review. International Journal of Dental Hygiene 6, 290-303, doi: 10.1111/j.1601-5037.2008.00344.x (2008).
19 Anacker, E. W. Light Scattering by Cetylpyridinium Chloride Solutions. The Journal of Physical Chemistry 62, 41-45, doi:10.1021/j150559a011 (1958).
20 Asker, D., Weiss, J. & McClements, D. J. Formation and stabilization of antimicrobial delivery systems based on electrostatic complexes of cationic-non-ionic mixed micelles and anionic polysaccharides. Journal of agricultural and food chemistry 59, 1041-1049, doi:10.1021/jf103073w (2011).
21 Hubner, N. O., Siebert, J. & Kramer, a. Octenidine dihydrochloride, a modern antiseptic for skin, mucous membranes and wounds. Skin pharmacology and physiology 23, 244-258, doi:10.1159/000314699 (2010).
22 Mirska, D. et al. Biophysical and biochemical properties of a binary lipid mixture for DNA transfection. Colloids and Surfaces B: Biointerfaces 40, 51-59, doi:10.1016/j.colsurfb.2004.10.007 (2005).
23 Connor, E. E., Mwamuka, J., Gole, A., Murphy, C. J. & Wyatt, M. D. Gold nanoparticles are taken up by human cells but do not cause acute cytotoxicity. Small 1, 325-327, doi:10.1002/sml1.200400093 (2005).
24 Takahashi, H. et al. Modification of gold nanorods using phosphatidylcholine to reduce cytotoxicity. Langmuir 22, 2-5, doi:10.1021/la0520029 (2006).
25 Cortesi, R., Esposito, E., Menegatti, E., Gambari, R. & Nastruzzi, C. Effect of cationic liposome composition on in vitro cytotoxicity and protective effect on carried DNA. International Journal of Pharmaceutics 139, 69-78, doi: 10.1016/0378-5173(96)04574-7 (1996).
26 Nicoletti, G., Boghossian, V., Gurevitch, F., Borland, R. & Morgenroth, P. The antimicrobial activity in vitro of chlorhexidine, a mixture of isothiazolinones ('Kathon' CG) and cetyl trimethyl ammonium bromide (CTAB). Journal of Hospital Infection 23, 87-111, doi:10.1016/0195-6701(93)90014-Q (1993).
27 Pinnaduwage, P., Schmitt, L. & Huang, L. Use of a quaternary ammonium detergent in liposome mediated DNA transfection of mouse L-cells. BBA—Biomembranes 985, 33-37, doi:10.1016/0005-2736(89)90099-0 (1989).
28 Muller, G. & Kramer, A. Biocompatibility index of antiseptic agents by parallel assessment of antimicrobial activity and cellular cytotoxicity. The Journal of antimicrobial chemotherapy 61, 1281-1287, doi:10.1093/jac/dkn125 (2008).
29 Ma, Q., Davidson, P. M. & Zhong, Q. Antimicrobial properties of lauric arginate alone or in combination with essential oils in tryptic soy broth and 2% reduced fat milk. International Journal of Food Microbiology 166, 77-84, doi:10.1016/j.ijfoodmicro.2013.06.017 (2013).
30 Martinez, V., Corsini, E., Mitjans, M., Pinazo, A. & Vinardell, M. P. Evaluation of eye and skin irritation of arginine-derivative surfactants using different in vitro endpoints as alternatives to the in vivo assays. Toxicology Letters 164, 259-267, doi:10.1016/j.toxlet.2006.01.005 (2006).
31 Van Landuyt, K. L. et al. Systematic review of the chemical composition of contemporary dental adhesives. Biomaterials 28, 3757-3785, doi:10.1016/j.biomaterials.2007.04.044 (2007).
32 Bourbia, M. & Ma, D. Cariogenic Bacteria Degrade Dental Resin Composites and Adhesives. Journal of dental . . . X, 1-7, doi:10.1177/0022034513504436 (2013).
33 Finer, Y. & Santerre, J. P. Salivary esterase activity and its association with the biodegradation of dental composites. Journal of dental research 83, 22-26 (2004).

34 Finer, Y. & Santerre, J. P. Influence of silanated filler content on the biodegradation of bisGMA/TEGDMA dental composite resins. Journal of Biomedical Materials Research Part A, 75-84, doi:10.1002/jbm.a (2007).

35 Finer, Y. & Santerre, J. P. The influence of resin chemistry on a dental composite's biodegradation. Journal of biomedical materials research. Part A 69, 233-246, doi:10.1002/jbm.a.30000 (2004).

We claim:

1. A method of making a composite material comprising the steps of, forming particles by providing a mixture of an amphiphilic biologically active agent, a metal oxide precursor and a solvent, wherein the amphiphilic biologically active agent is present in an amount sufficient to self-assemble into a micellar system, and wherein the metal oxide condenses around the micellar system, and dispersing the particles comprising the biologically active agent in a resin, wherein the biologically active agent comprises octenidine or a salt thereof.

2. The method of claim 1 wherein the resin comprises a methacrylate-based polymer or a urethane-based polymer.

3. The method of claim 1 wherein the resin comprises any one or more resins selected from the group consisting of: hydroxyethyl methacrylate, bisphenylglycidyl dimethacrylate, and triethylene glycol dimethacrylate.

* * * * *